(12) United States Patent
Reynolds

(10) Patent No.: US 12,303,548 B2
(45) Date of Patent: May 20, 2025

(54) COMPLEXES FOR TREATING SENSITIVITY

(71) Applicant: THE UNIVERSITY OF MELBOURNE, Victoria (AU)

(72) Inventor: Eric Charles Reynolds, Victoria (AU)

(73) Assignee: The University of Melbourne, Victoria (AU)

( * ) Notice: Subject to any disclaimer, the term of this patent is extended or adjusted under 35 U.S.C. 154(b) by 486 days.

(21) Appl. No.: 16/492,903

(22) PCT Filed: Mar. 14, 2018

(86) PCT No.: PCT/AU2018/050230
§ 371 (c)(1),
(2) Date: Sep. 10, 2019

(87) PCT Pub. No.: WO2018/165707
PCT Pub. Date: Sep. 20, 2018

(65) Prior Publication Data
US 2020/0197486 A1 Jun. 25, 2020

(30) Foreign Application Priority Data
Mar. 14, 2017 (AU) .................. 2017900892

(51) Int. Cl.
| | | |
|---|---|---|
| A61K 38/17 | (2006.01) | |
| A61K 8/21 | (2006.01) | |
| A61K 8/24 | (2006.01) | |
| A61K 8/64 | (2006.01) | |
| A61K 9/00 | (2006.01) | |
| A61K 33/06 | (2006.01) | |
| A61K 33/16 | (2006.01) | |
| A61K 33/24 | (2019.01) | |
| A61K 33/42 | (2006.01) | |
| A61K 38/00 | (2006.01) | |
| A61P 1/02 | (2006.01) | |
| A61Q 11/00 | (2006.01) | |

(52) U.S. Cl.
CPC ............ *A61K 38/1709* (2013.01); *A61K 8/21* (2013.01); *A61K 8/24* (2013.01); *A61K 8/64* (2013.01); *A61K 33/06* (2013.01); *A61K 33/16* (2013.01); *A61K 33/24* (2013.01); *A61K 33/42* (2013.01); *A61K 38/00* (2013.01); *A61P 1/02* (2018.01); *A61Q 11/00* (2013.01); *A61K 9/0053* (2013.01); *A61K 2800/58* (2013.01)

(58) Field of Classification Search
None
See application file for complete search history.

(56) References Cited

U.S. PATENT DOCUMENTS

| | | |
|---|---|---|
| 3,864,471 A | 2/1975 | King et al. |
| 3,966,901 A | 6/1976 | Cullum et al. |
| 4,080,440 A | 3/1978 | Digiulio et al. |
| 4,157,386 A | 6/1979 | La Rochelle |
| 4,357,318 A | 11/1982 | Shah et al. |
| 4,522,805 A | 6/1985 | Gordan |
| 4,588,763 A | 5/1986 | Brannstrom et al. |
| 4,672,032 A | 6/1987 | Slavkin et al. |
| 5,015,628 A | 5/1991 | Reynolds et al. |
| 5,227,154 A | 7/1993 | Reynolds |
| 5,427,769 A | 6/1995 | Berrocal et al. |
| 5,447,732 A * | 9/1995 | Tanimoto ............... A23C 9/152 426/74 |
| 5,520,725 A | 5/1996 | Kato et al. |
| 5,833,953 A | 11/1998 | Berrocal et al. |
| 5,981,475 A | 11/1999 | Reynolds |
| 6,036,944 A | 3/2000 | Winston et al. |
| 6,056,930 A | 5/2000 | Tung |
| 6,120,754 A | 9/2000 | Lee et al. |
| 6,149,894 A | 11/2000 | Yamane et al. |
| 6,214,101 B1 | 4/2001 | Nakaseko |
| 6,652,875 B1 | 11/2003 | Bannister |
| 6,780,844 B1 | 8/2004 | Reynolds |
| 7,312,193 B2 | 12/2007 | Reynolds et al. |
| 7,491,694 B2 | 2/2009 | Reynolds et al. |
| 8,354,117 B2 | 1/2013 | Tsunekawa et al. |
| 8,603,988 B2 | 12/2013 | Reynolds |
| 8,609,071 B2 | 12/2013 | Reynolds |
| 8,673,363 B2 | 3/2014 | Reynolds |

(Continued)

FOREIGN PATENT DOCUMENTS

| | | |
|---|---|---|
| AU | 718253 | 7/1997 |
| CN | 104001157 A * | 8/2014 |

(Continued)

OTHER PUBLICATIONS

JPO English abstract for JP 2005-145952 (Year: 2005).*
Machine-assisted English translation for JP 2005-145952 (Year: 2005).*
White DJ. A "return" to stannous fluoride dentifrices. J Clin Dent. 1995;6 Spec No. 29-36.*
Zhang H, Nakamura S, Kitts DD. Antioxidant Properties of Casein Phosphopeptides (CPP) and Maillard-Type Conjugated Products. Antioxidants (Basel). Jul. 22, 2020;9(8):648.*
English translation for CN 104001157A (Year: 2014).*
Vegarud et al "Mineral-binding milk proteins and peptides; occurrence, biochemical and technological characteristics", British Journal of Nutrition (2000), vol. 84, Suppl. 1, p. S91-S98. (Year: 2000).*

(Continued)

*Primary Examiner* — Sin J Lee
(74) *Attorney, Agent, or Firm* — Foley & Lardner LLP

(57) ABSTRACT

The present invention relates to improved phosphopeptide stabilised amorphous calcium phosphate and/or amorphous calcium fluoride phosphate complexes and compositions containing those complexes. Methods of making the complexes of the invention and of treatment dental hypersensitivity are also provided. In one embodiment, the invention provides a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP.

19 Claims, 6 Drawing Sheets

Specification includes a Sequence Listing.

(56) References Cited

U.S. PATENT DOCUMENTS

| | | | |
|---|---|---|---|
| 9,295,628 | B2 | 3/2016 | Reynolds |
| 9,668,945 | B2 | 6/2017 | Reynolds |
| 10,695,370 | B2 | 6/2020 | Reynolds |
| 10,912,722 | B2 | 2/2021 | Reynolds |
| 11,351,193 | B2 | 6/2022 | Reynolds |
| 11,504,305 | B2 | 11/2022 | Reynolds |
| 11,564,873 | B2 * | 1/2023 | Reynolds ............... A61Q 11/00 |
| 11,717,536 | B2 | 8/2023 | Reynolds |
| 11,717,537 | B2 | 8/2023 | Reynolds |
| 2002/0028251 | A1 | 3/2002 | Okay |
| 2002/0071858 | A1 | 6/2002 | Luo et al. |
| 2003/0124066 | A1 | 7/2003 | Dixon, Jr. et al. |
| 2003/0152525 | A1 | 8/2003 | Dixon, Jr. et al. |
| 2003/0165442 | A1 | 9/2003 | Baig et al. |
| 2005/0063922 | A1 | 3/2005 | Reynolds et al. |
| 2005/0089481 | A1 | 4/2005 | Yamanaka et al. |
| 2005/0100581 | A1 | 5/2005 | Laurencin et al. |
| 2005/0118115 | A1 | 6/2005 | Fontenot |
| 2006/0183081 | A1 | 8/2006 | Bevilacqua et al. |
| 2007/0071858 | A1 | 3/2007 | Succar et al. |
| 2007/0254260 | A1 | 11/2007 | Alden |
| 2008/0075675 | A1 | 3/2008 | Reynolds |
| 2008/0171001 | A1 | 7/2008 | Engelman et al. |
| 2008/0193557 | A1 | 8/2008 | Reynolds et al. |
| 2009/0016972 | A1 | 1/2009 | Manasherov et al. |
| 2009/0022672 | A1 | 1/2009 | Reynolds |
| 2009/0324662 | A1 | 12/2009 | Kutsch et al. |
| 2010/0028273 | A1 | 2/2010 | Fischer et al. |
| 2011/0076241 | A1 | 3/2011 | Kato et al. |
| 2012/0100194 | A1 | 4/2012 | Yamai et al. |
| 2012/0129135 | A1 | 5/2012 | Yang et al. |
| 2013/0129641 | A1 | 5/2013 | Sadeghpour et al. |
| 2014/0147512 | A1 | 5/2014 | Reynolds |
| 2016/0158283 | A1 | 6/2016 | Reynolds |
| 2016/0317404 | A1 | 11/2016 | Reynolds |
| 2017/0333296 | A1 | 11/2017 | Reynolds |
| 2018/0008518 | A1 | 1/2018 | Reynolds |
| 2020/0054672 | A1 | 2/2020 | Reynolds |
| 2020/0246378 | A1 | 8/2020 | Reynolds |
| 2021/0161778 | A1 | 6/2021 | Reynolds |
| 2022/0183810 | A1 | 6/2022 | Reynolds |
| 2023/0404867 | A1 | 12/2023 | Reynolds |

FOREIGN PATENT DOCUMENTS

| | | |
|---|---|---|
| CN | 1040011574 A | 8/2014 |
| EA | 011125 B1 | 12/2008 |
| EP | 0 786 245 A1 | 7/1997 |
| EP | 1 525 878 A1 | 4/2005 |
| EP | 1 525 878 B1 | 3/2007 |
| EP | 1 952 801 A1 | 8/2008 |
| EP | 2 301 513 A2 | 3/2011 |
| EP | 2 353 576 A1 | 8/2011 |
| JP | 8-143436 A | 6/1996 |
| JP | 10-290682 A | 11/1998 |
| JP | H11-228327 A | 8/1999 |
| JP | 11-310599 | 11/1999 |
| JP | 3742523 | 11/1999 |
| JP | 2001-144695 | 11/2002 |
| JP | 2004-215521 A | 8/2004 |
| JP | 2005-112841 | 4/2005 |
| JP | 2005-145952 | 6/2005 |
| JP | 2005-145952 A | 6/2005 |
| JP | 2010-047494 A | 3/2010 |
| JP | 2011-032250 A | 2/2011 |
| JP | 2013-163656 A | 8/2013 |
| WO | WO 1982/003008 | 9/1982 |
| WO | WO 1987/007615 | 12/1987 |
| WO | WO 1993/003707 | 3/1993 |
| WO | WO 1994/00146 | 1/1994 |
| WO | WO 1996/029340 | 9/1996 |
| WO | WO 1997/036943 | 10/1997 |
| WO | WO 1997/040811 | 11/1997 |
| WO | WO 98/40406 | 9/1998 |
| WO | WO 2000/006108 | 2/2000 |
| WO | WO 2000/057842 A1 | 10/2000 |
| WO | WO 2000/057892 | 10/2000 |
| WO | WO 2001/044106 A1 | 6/2001 |
| WO | WO-02/094204 A1 | 11/2002 |
| WO | WO 2003/059303 A2 | 7/2003 |
| WO | WO 2003/059304 A1 | 7/2003 |
| WO | WO 2004/035077 A1 | 4/2004 |
| WO | WO 2004/054531 A1 | 7/2004 |
| WO | WO-2004/060336 A1 | 7/2004 |
| WO | WO-2006/056013 A1 | 6/2006 |
| WO | WO-2006/130913 A1 | 12/2006 |
| WO | WO-2006/135982 A1 | 12/2006 |
| WO | WO-2007/090242 A1 | 8/2007 |
| WO | WO-2009/099452 | 8/2009 |
| WO | WO 2009/130447 A1 | 10/2009 |
| WO | WO-2010/134904 A1 | 11/2010 |
| WO | WO-2012/100991 | 8/2012 |
| WO | WO-2013/117913 | 8/2013 |
| WO | WO-2014/050144 | 4/2014 |
| WO | WO-2015/010166 A1 | 1/2015 |
| WO | WO-2015/095932 A1 | 7/2015 |
| WO | WO-2016/101041 | 6/2016 |
| WO | WO-2018/165707 A1 | 9/2018 |
| WO | WO-2018/165708 A1 | 9/2018 |

OTHER PUBLICATIONS

Min Song et al., "Progress in the treatment of dentin hypersensitivity", Anhui Medical and Pharmaceutical Journal, pp. 1521-1523 (Oct. 2012).

Office Action issued on Jan. 21, 2022, in Chinese Application No. 2022011802819660.

Office Action issued on Jan. 25, 2022, in Japanese Application No. 2019-550158.

U.S. Appl. No. 16/852,983, filed Apr. 20, 2020, Eric Charles Reynolds.

Denes and Lazanas, "Oxidation of SnF2 stannous fluoride in aqueous solutions," Hyperfine Interact 90, 435-439 (1994).

Minimale Intervention für maximale Mundgesundheit, DZW Special. Mar. 2005 *English Abstract).

Sim et al., "Anti-caries effect of CPP-ACP in irradiated nasopharyngeal carcinoma patients," Clinical Oral Investigations, (2015), vol. 19, No. 5, pp. 1005-1011.

Westerman, G. et al., "The Argon Laser and Remineralizing Paste with Fluoride Effects on Enamel Caries," AAPD, Washington, 2008.

"Caseine phosphopeptide et phosphate de calcium amorphe: un complexe prometteur," Dialogue dentaire, Printemps 2005/W30, pp. 27-29. English Abstract provided.

"Colorimetry" Second Edition. By CIE Technical Committee. CIE 1986.

"Editors' Choice—Prospec MI Paste," The Dental Advisor, vol. 22, No. 5, Jun. 2005.

"GC Tooth Mousse—Eine ganz andere Art der Prävention," Dental Spiegel, Feb. 2005, pp. 53-54. English Abstract.

"Putting mouths where the money is.", DPRAsia, Jan./Feb. 2007, pp. 8-10.

"Tooth Mousse." Pierre qui roule n 'amasse pas mousse? Ben si! Clinic—Apr. 2006—vol. 27, p. 218-219, English Abstract provided.

"Tradition und moderns know how—ein Erfolgsrezept.", Zahn Prax 8, vol. 5, 2005, p. 267. English Abstract.

Adamson et al., "Characteriztion of Tryptic Casein Phosphopeptides Prepared Under Industrially Relevant Conditions", Biotec. Bioeng., 45, pp. 196-204 (Feb. 1995).

Adamson et al., "High Performance Capillary Electrophoresis of Casein Phosphopeptides Containing 2-5 Phosphoseryl Residues; Relationship Between Absolute Electrophoretic Mobility and Peptide Charge and Size", Electrophoresis 16: pp. 525-528 (1995).

Adamson, et al., "Characterization of Casein Phosphopeptides Prepared Using Alcalase: Determination of Enzyme Specificity," *Enzyme and Microbial Tech.*, 19, pp. 202-207 (Aug. 1996).

Adamson, et al., "The Analysis of Multiple Phosphoseryl-containing Casein Peptides using Capillary Zone Electrophoresis," *J. of Chromatography*, 646, pp. 391-396 (Jun. 1993).

(56) References Cited

OTHER PUBLICATIONS

Adebayo, O.A. et al. "Effects of conditioners on microshear bond strength to enamel after carbamide peroxide bleaching and/or casein phosphopeptide-amorphous calcium phosphate (CPP-ACP) treatment", Journal of Dentistry, vol. 35, 2007, pp. 862-870 (Aug. 2007).
Akinmade et al., "Review Glass-Ionomer Cements as Adhesives, Part I, Fundamental Aspects and Their Clinical Relevance," Journal of Materials Science: Materials in Medicine, vol. 4, pp. 95-101 (1993).
Allais, G. "Karies—Die Therapie", Continuing Dental Education, pp. 716-735 (Jun. 2007), English Abstract provided.
Al-Zraikat, H. et al. "Development of GIC incorporating Caesin Phosphopetide amorphous phosphate (CPP ACP) complex.", Australian Dental Journal ADRF Special Research Supplement, vol. 52, p. S4., (2007).
Al-Zraikat, H. et al. "Incorporation of casein-phosphopeptide-amorphous calcium phosphate into glass ionomer cement." Abstract 0654—84th General Session of the IADR, Jun. 28-Jul. 1, 2006, Brisbane, Australia.
Angmar et al., "Studies on the Ultrastructure of Dental Enamel"; J. Ultrastructure Research, 8, pp. 12-23 (1963).
Aoba et al. "Dental Fluorosis: Chemistry and Biology." Crit. Rev Oral Biol. Med. 13 (2) pp. 155-170 (2002).
Ardu et al., "A minimally invasive treatment of severe dental fluorosis"; Quintessence International; 38(6), pp. 455-458 (Jun. 2007).
Ardu, S. et al. "Minimally invasive treatment of white spot enamel lesions.", Quintessenz International, vol. 38, No. 8, pp. 633-636 (Sep. 2007).
Aytepe, Z. et al. "Effect of CCP-ACP on oral health of cerebral palsy children.", Abstract 3343, Jul. 2008, International Association for Dental Research, Toronto, Canada.
Baig, et al., "HAP Dissolution Study II: $SnF_2$ vs. NaF Dentifrice Study," 87th Session of the IADR (International & American Associations for Dental Research) Apr. 1-4, 2009 [on line], [retrieved on Oct. 21, 2014]. Retrieved from internet ,URL: dentalcare.com/media/en-US/research_ db/pdf/, p. 24.
Bavetta et al., "Protein Factors and Experimental Rat Caries", Journal of Nutr. 63: pp. 107-117 (1957).
Benzian et al., "Total and free available fluoride in toothpastes in Brunei, Cambodia, Laos, the Netherlands and Suriname"; International Dental Journal, 62, pp. 213-221 (2012).
Biesbrock, A.R. et al. "Reversal of Incipient and Radiographic Caries Through The Use of Sodium and Stannous Fluoride Dentifrices in a Clinical Trial." The Journal of Clinical Dentistry vol. IX, No. 1, pp. 5-10 (Feb. 1998).
Biesbrock, Aaron R. "Relative anti-caries efficacy of 1100, 1700, 2200, and 2800 ppm fluoride ion in a sodium fluoride dentifrice over 1 year." Community Dentistry and Oral Epidemiology; 29, pp. 382-389 (Jan. 2001).
Biesbrock, Aaron R. et al. "Dose response efficacy of sodium fluoride dentrifrice at 9 and 21 months with supervised brushing." American Journal of Dentistry, vol. 16, No. 5, 9. 305-312 (Oct. 2003).
Black et al. "Mottled Teeth" The Dental Cosmos. vol. LVIII. No. 2., pp. 129-156 (Feb. 1916).
Burwell, A.K. et al. "Dentifrice Protection Against Dentin Demineralization in an In Vitro Study.", Abstract 1764, IADR, New Orleans, USA (Mar. 2007).
Burwell, A.K. et al. "Quantitative Tubule Occlusion in an In Vitro Remineralization/Demineralization Model.", Abstract 0568, EADR 2006, Dublin, Ireland (Sep. 2006).
Cai et al. "Remineralization of Enamel Subsurface Lesions in Situ by Sugar-Free Lozenges Containing Casein Phosphopeptide-Amorphous Calcium Phosphate", Aus. Dent. J., 48: 4, pp. 240-243 (2003).
Cai, F. et al. "Effect of Addition of Citric Acid and Casein Phosphopeptide-Amorphous Calcium Phosphate to a Sugar-free chewing gum on Enamel Remineralization in Situ.", Caries Research, vol. 41, pp. 377-383 (Feb. 2007).
Cai, F. et al. "Remineralization by chewing gum containing CPP-ACP and citric acid." Abstract 190—84th General Session of the IADR, Brisbane, Australia, pp. 240-243 (Jun. 28, 2006-Jul. 1, 2006).
Calcium Glycerophosphate, DrugBank, pp. 1-5, XP002783472 (created Mar. 12, 2015) (retrieved Jul. 31, 2018).
CAPLUS Copyright 2005. "NMR studies of a novel Calcium, phosphate and fluoride delivery vehicle <SYM97> S1-casein( 59-79) by stabilized amorphous calcium fluoride phosphate nanocomplexes."
Carrillo, Dr. J et al. "Nuevos avances tecnológicos en Odontologia Conservadora", La Gaceta Dental, 193:213, pp. 218-219 (Jun. 2008), English Abstract.
Chalmers, J. et al. "Minimal Intervention Dentistry in the New Millennium," Dentaltown, pp. 54 (Feb. 2008).
Chalmers, J.M. "Minimal intervention dentistry: part I. Strategies for addressing the new caries challenge in older patients." JCDA, 72(5), pp. 427-433 (Jun. 2006).
Chelariu, C. et al. "Nuove prospettive nella prevenzione della carie Congresso Nazionale del Collegio dei Docenti di Odontoiatria Roma", Apr. 5-7, 2006, Poster session, published by "Doctor Os", No. 3, Mar. 2006. English Abstract.
Chen, L. et al. "Calcium Release and Mechanical Properties of Experimental Calcium-Releasing Composites.", Abstract 2572, IADR, New Orleans, USA (Mar. 2007).
Cipolla, M. et al. "Fluoride and Calcium-Phosphate Effects on Fracture Toughness of Bleached Dentin.", Abstract 1032, Toronto, Canada (Jul. 2008).
Coates, L. "Tooth mousse shows some unexpected beneficial side effects." Dental Asia (Nov./Dec. 2004), pp. 40-43.
Cochrane, N.J. et al. "QLF and TMR analysis of CPP-ACFP remineralized enamel in vitro.," Abstract 192—84th General Session of the IADR, Brisbane, Australia (Jun. 28, 2006-Jul. 1, 2006).
Comar et al., "Effect of NaF, $SnF_2$, and $TiF_4$ Toothpastes on Bovine Enamel and Dentin Erosion-Abrasion In Vitro," International Journal of Dentistry, vol. 2012, Article IDS 134350, pp. 1-6 (Oct. 2012).
Crisp, S., "Glass Ionomer Cement: Chemistry of Erosion", J. Dent. Res. 55: 1032-1041 (Apr. 1976).
Cross et al. "Casein Phosphopeptide-Amorphous Calcium Phosphate Nanocomplexes: A Model of the Casini Micelle Core," Centre for Oral Health Science, School of Dental Science, The University of Melbourne, pp. 1-42, (Aug. 2008).
Cross et al., "Cation-Dependent Structural Features of Beta-Casein—(1-25)", Biochem. J. (May 15, 2001), 356: Pt 1, pp. 277-286.
Cross et al., "NMR Studies of a Novel Calcium, Phosphate and Fluoride Delivery Vehicle—The Multiphosphorylated Peptide Alpha S1-Casein (59-79) Complexed with Amorphous Calcium Fluoride Phosphate", Biomaterials., vol. 25, pp. 5061-5069 (Jan. 2004).
Cross et al., "Structural Studies of the b-Casein Phosphopeptide Bound to Amorphous Calcium Phosphate", IADR, General Session, J. Dent. Res. Vo. 80, p. 580 Chiba, Abstract 0490, (2001). (IADR Abstracts).
Cross et al., "Ultrastructural Studies of the Casein Phosphopeptide-Amorphous Calcium Phosphate Nanoclusters", IADR, General Session, Chiba, Abstract 0491, (2001). (IADR Abstracts).
Cross, et al. "Physicochemical Characterization of Casein Phosphopeptide-Amorphous Calcium Phosphate Nanocomplexes." The Journal of Biological Chemistry, vol. 280, No. 16. 15362-15369 (Apr. 2005).
Cross, K.J. et al. Structure and $^{15}$N-Dynamics of casein phosphopeptide-amorphous calcium phosphate nanocomplexes. Abstract 2534—84th General Session of the IADR, Jun. 28-Jul. 1, 2006, Brisbane, Australia.
Cross, KJ et al. "Casein Phosphopeptides in Oral Health—Chemistry and Clinical Applications", Current Pharmaceutical Design, vol. 13, pp. 793-800 (2007).
Cross, KJ et al. "Structural Characterization of anticariogenic casein Phosphopeptide alphas2 casein(46-70) complexed with amorphous calcium phosphate.", Aust Dent J ADRF Special Research Supplement 52(4):S10-S11 (2007).
Cross, KJ et al. "Structural Characterization of Beta-casein(1-25)-ACFP Complex.", Aust Dent J ADRF Special Research Supplement, vol. 52, No. 4, S12, (2007).

(56) References Cited

OTHER PUBLICATIONS

Curnow, M.M.T., et al. "A Randomised Controlled Trial of the Efficacy of Supervised Toothbrushing in High-Caries-Risk Children." Carie Research; 36:294-300 (Mar. 2002).
Database WPI Week 200316, Thomason Scientific, London, GB; 2003-165149, XP002537968 & SE 0 100 558 A, Mediteam Dental AB, Aug. 21, 2002, Abstract.
Davies, G.M., "A randomized controlled trial of the effectiveness of providing free fluoride toothpaste from the age of 12 months on reducing caries in 5-6 year old children." Community Dental Health 19, 131-136 (2002).
Deangelis et al., "Molecular modelling of anticariogenic Casein Phosphopeptide AS2-CN (2-20) NMR Spectroscopy Derived Constraints", Abstract 2997—82$^{nd}$ General Session of the IADR, Mar. 2004, Honolulu, Hawaii.
Denbesten, P.K. et al. "Biological Mechanisms of Fluorosis and Level and Timing of Systemic Exposure to Fluoride with Respect to Fluorosis." J. Dent Re 71(5): pp. 1238-1243 (May 1992).
Donovan, T. "Protocol for the prevention and management of root caries.", Journal Compilation, vol. 20, No. 6, pp. 405-411 (2008).
Duckworth, R.M. "Effects of Mouthwashes of Variable NaF Concentration but Constant NaF Content on Oral Fluoride Retention." Caries Research 1994; 28, pp. 43-47 (1994).
Duckworth, R.M. "Oral Fluoride Measurements for Estimation of the Anti-caries Efficacy of Fluoride Treatments." J Dent Res., vol. 71, pp. 836-840 (Apr. 1992).
Fahad, et al., "Effect of casein phosphopeptide-amorphous calcium phosphate on the microhardness and microscopic features of the sound enamel and initial caries-like lesion of permanent teeth, compared to fluoridated agents," Journal of Baghdad College Dentistry, vol. 24, No. 4, pp. 114-120 (2012).
Featherstone, Job et al. "An in situ model for simultaneous assessment of inhibition of demineralization and enhancement of Remineralization." J Dent Res vol. 71 (Spec. Iss.), pp. 804-810 (Apr. 1992).
Feinmann, J. "This won't hurt a bit," The Times, Saturday, 2 pages, Mar. 12, 2005.
Fejerskov et al. "Dental fluorosis—a handbook for health workers." Munksgaard, Copenhagen, pp. 32-77 (copyright 1988).
Fejerskov et al. "Fluoride in Dentistry $2^{nd}$ edition." Munksgaard, Copenhagen, pp. 112-152 (Copyright 1996).
Fejerskov et al. "Posteruptive changes in human dental fluorosis—a histological and ultrastructural study." Pro Finn Dent Soc vol. 87, No. 4, pp. 607-619 (1991).
Fejerskov et al. "The Nature of Mechanisms of Dental Fluorosis in Man." J Dent Res 69 (Spec Iss) pp. 692-700 (Feb. 1990).
Ferrazzano, G. et al. "Protective effect of yogurt extract on dental enamel demineralization in vitro," Australian Dental Journal, vol. 53, pp. 314-319 (Feb. 2008).
Ferrazzano, G.F. et al. "New Strategies in dental caries prevention: experimental study on casein phosphopetide.", European Journal of Paedetric Dentistry, 4, pp. 183-187 (Apr. 2007).
Ferrazzano, G.F. et al. "Nuove strategie nella prevenzione della carie dentaria:studio sperimentale sui caseinofosfopeptidi." Prevenzione Odontostomatologica vol. 4, 2005, pp. 15-21. English Abstract.
Freml, L. et al. "Efficacy of Hypersensitivity Agents on Demineralization under Provisional Crowns." Abstract 1346, IADR Mar. 2007, New Orleans, USA.
Fuller, B.L. et al. "Efficacy of MI Paste in Preventing Demineralization in Overdenture Abutments," Abstract 0503, IADR Mar. 2007, New Orleans, USA.
Gagnaire et al., "Phosphopeptides interacting with colloidal calcium phosphate isolated by tryptic hydrolysis of bovine casein micelles", Journal of Dairy Research (Feb. 1996), 63, pp. 405-422.
Gandolfi, M. et al. "Calcium silicate coating derived from Portland cement as treatment for hypersensitive dentine", Journal of Dentistry, vol. 36, 2008, pp. 565-578.
GC America, Inc. "MI Paste™ and MI Paste Plus™ with Recaldent™ (CPP-ACP)" Inside Dentistry, Oct. 2012, vol. 8, No. 10 [online], [retrieved on Oct. 21, 2014]. Retrieved from internet, URL: www.dentalaegis.com/id/201 21 1 O/mi-paste-and-mi-paste-p 1 us-with-recaldent-cpp-acp>, 6 pages.
GC stellt Kasein-haltige Zahnschutzcreme vor—Vorbeugen statt reparieren DZW Special IDS-Nachlese. 2005. English Abstract, pp. 10-11.
Giambro, N.J. et al. "Characterization of Fluorosed Human Enamel by Color Reflectance, Ultrastructure, and Elemental Composition." Caries Res. Issue 29 (Jan. 1995) pp. 251-257.
Giniger et al. "A 180-Day Clinical Investigation of the Tooth Whitening Efficacy of a bleaching Gel with Added Amorphous Calcium Phosphate." J. of Clinical Dentistry. vol. XVI. No. 1. 2005. pp. 11-16.
Giniger et al. "The clinical performance of professionally dispensed bleaching gel with added amorphous calcium phosphate." JADA. vol. 136. Mar. 2005. pp. 383-392.
Gisselsson, H., et al., "Effect of professional flossing with NaF or $SnF_2$ gel on approximal caries in 13-16-year-old schoolchildren". Acta Odontologica Scandinavica, vol. 57, No. 2, pp. 121-125 (Jan. 1999).
Gugnani, S. et al. "Comparative evaluation of two commercially available 8odems8te8pha agents after scaling and root planning: an in vivo study", PERIO, vol. 5, No. 2, 2008, pp. 121-129.
Haderlie, D.D. et al. "MI Paste and Fluoride effects on Secondary Caries.", Abstract 0504, IADR Mar. 2007, New Orleans, USA.
Harper et al., "Cariostatic Evaluation of Cheeses with Diverse Physical and Compositional Characteristics", Caries Res. 20: pp. 123-130 (1986).
Harper et al., "Modification of Food Cariogenicity in Rats by Mineral-Rich Concentrates from Milk", J. Dent Res. 66: pp. 42-45 (Jan. 1987).
Hartshone, JE. "The relationship between plaque index scores, fluoride content of plaque, plaque pH, dental caries experience and fluoride concentration in drinking water in a group of primary school children." Journal of the Dental Association of South Africa, 49, pp. 5-10, Jan. 1994.
Hay et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod. (Mar. 2002); 93: pp. 271-275, 2002.
Hicks, J. et al. "Biological factors in dental caries: role of remineralization and fluoride in the dynamic process of demineralization and remineralization (part 3)." The Journal of Clinical Pediatric Dentistry. vol. 28, No. 3, pp. 203-214 (2004).
Hicks, J. et al. "Casein Phosphopeptide-Amorphous calcium phosphate paste: root surface caries formation," Abstract 3275—IADR, Mar. 2005, Baltimore, Maryland, USA, Abstract.
Hidaka, et al., "A New Method for Study of the Formation and Transformation of Calcium Phosphate Precipitates: Effects of Several Chemical Agents and Chinese Folk Medicines," *Archives of Oral Biol.*, 36:1, pp. 49-54 (1991).
Holler, B. E. et al. "Fluoride uptake and distribution in enamel and dentin after application of different fluoride solutions." Clin Oral Invest, vol. 6, 2002, pp. 137-144.
Holloway et al., "Effects of Various Sucrose-Casein Ratios in Purified Diets on the Teeth and Supporting Structures of Rats", Arch Oral Bioi. 3: pp. 185-200 (1961).
Holt, Carl. "An equilibrium thermodynamic model of the sequestration of calcium phosphate by casein micelles and its application to the calculation crème partition of salts in milk." European Biophysics Journal. (Jan. 2004) pp. 421-434.
Holt, et al., "Ability of a b-casein Pho/sphopeptide to Modulate the Precipitation of Calcium Phosphate by Forming Amorphous Dicalcium Phosphate Nanoclusters," *Biochem J.*, 314, 1035-1039 (1996).
Huang, A. et al. "Remineralization of eroded teeth using CPP-ACP paste," Abstract 3267, Jul. 2008, International Association for Dental Research, Toronto, Canada.
Huq et al., "Molecular Modeling of the Multiphosphorylated Sequence Motif Bound to Hydroxyapatite Surfaces" (59-79), J. Mol. Mode (Feb. 2000), 6:35-47.
Huq et al., "Molecular Modelling of the Multiphosphorylated Casein Phosphopeptide Alpha S1-Casein (59-79) based on NMR constraints," J. Dairy Res. 71:28-32 (2004).

(56) References Cited

OTHER PUBLICATIONS

Huq, et al. "Nascent Helix in the Multiphosphorylated Peptide $a_{s2}$-Casein(2-20)." Journal of Peptide Science, (2003) pp. 386-392.

Huq, et al., A H-NMR Study of the Casein Phosphopeptide $a_{s1}$ Casein (59-79) Biochimica et Biophysica Acta, 1247, 201-208 (1995).

Iijima et al., "Acid Resistance of Enamel Subsurface Lesions Remineralized by a Sugar-Free Chewing Gum Containing Casein Phosphopeptide-Amorphous Calcium Phosphate (CPP-ACP)", Caries, Res. Jan. 2004; 38: pp. 551-556.

Iijima, Y. et al. "Acid resistance of remineralized enamel by a sugar-free chewing gum.", Abstract 184—84$^{th}$ General Session of the IADR, Jun. 28-Jul. 1, 2006, Brisbane, Australia.

Imfeld, "Prevention of progression of dental erosion by professional and individual prophylactiv measures," Eur J Oral Sci (1996) 104:215-220.

Inaba, D et al. "Effect of Sodium Hypochlorite Treatment on Remineralization of Human Root Dentine in vitro." Caries Research 1996, vol. 30 pp. 218-224.

Inaba, D. et al. "Intraoral changes in NaOCl-treated Root Dentin Lesions: A Pilot Study.", J. Dental Health, vol. 50, Jul. 2000, pp. 824-826. Abstract.

International Search Report issued on Sep. 25, 2016 in application No. PCT/AU2006/000885.

International Search Report issued on Sep. 15, 2014 in application No. PCT/AU2014/050144.

Japanese Examination Report for corresponding Japanese Patent Application No. 2008-515000 mailed Mar. 7, 2013. English Translation.

Kandelman, D et al. "A 24-month clinical study of the incidence and progression of dental caries in relation to consumption of chewing gum containing xylitol in school preventive programs." J Dent Res vol. 69(11), Nov. 1990, pp. 1771-1775.

Kariya et al., "Fluoride Effect on Acid Resistance Capacity of CPP-ACP Containing Material", Abstract 2045—82$^{nd}$ General Session of the IADR, (Mar. 2004), Honolulu, Hawaii. Abstract.

Kariya, S. et al. "Remineralization of enamel lesion by a novel cream with both CPP-ACP and fluoride," Poster session 136—54$^{th}$ Annual ORCA Congress, 2007. Abstract.

Keçik, D. et al. "Effect of Acidulated Phosphate Fluoride and Casein Phosphopeptide-Amorphous Calcium Phosphate Application on Shear Bond Strength of Orthodontic Brackets." Angle Orthodontist, vol. 78, No. 1, 2008, pp. 129-133.

Khan, Dr. S. "White Spots on Teeth", Buzzle.com Intelligent Life on the Web, Jan. 2010.

Kim, K. et al. "Remineralization of the artificial caries lesion using CPP-ACP and fluoride.", Abstract 3280, Jul. 2008, International Association for Dental Research, Toronto, Canada.

Kowalczyk et al. "Evaluation of the product based on Recaldent™ technology in the treatment of dentin hypersensitivity.", Advances in Medical Sciences, vol. 51 suppl 1, 40-42, Mar. 2006.

Krobicka et al., "The Effects of Cheese Snacks on Caries in Desalivated Rats", J. Dent Res. 66:1116-19, (Jan. 1987).

Kumar, VILN et al. "The effect of casein phosphopeptide-amorphous calcium phosphate on remineralization of artificial caries-like lesions: an in vitro study.", Australian Dental Journal, vol. 53, 2008, pp. 34-40.

Larsson, K. S., et al. "Fluoride concentration in plaque in adolescents after topical application of different fluoride varnishes." Clin Oral Invest. (2000) 4:31-34.

Lasfargues, J. et al. "La remineralisation des lesions carieuses (2) synergies therapautiques Realites Cliniques.", vol. 15, No. 3, 2004 pp. 261-275. English Abstract.

Legeros, RZ "Calcium phosphates in demineralization/remineralization processes." J Clinical Dent X, 1999, pp. 65-73.

Lewis, J. "Brush, floss and mousse?" Women Dentistry Journal, Winter 2005, vol. 2, Issue 4, 18-19.

Little, Elaine et al. "An equilibrium thermodynamic model of the sequestration of calcium phosphate by casein phosphopeptides." European Biophysics Journal. (Jan. 2004) 33, 435-447.

Loesche, WJ "Role of *Streptococcus* mutans in human dental decay." Microbial. Rev. vol. 50(4), Dec. 1950, pp. 353-380.

Lynch, R.J.M. et al, "Low-Levels of Fluoride in plaque and saliva and their effect on the demineralization and remineralisation of enamel; role of fluoride of toothpastes." International Dental Journal (2004) vol. 54/ No. 5, 304-309.

Malcmacher, L. "Enamel Remineralization: The Medical Model of Practicing Dentistry.", Dentistry Today, Nov. 2006, 4 pages.

Malcmacher, L. "Vitamins for teeth.", Common Sense Dentistry, Dental economics Oct. 2006, 130 and 144.

Manton, D. "Dental Caries: Where to From Here?", Ann Roy Austral Coll Dent Surg, vol. 19, 2008, pp. 73-76.

Manton, D. et al. "Effect of ozone and Tooth Mousse™ on the efficacy of peroxide bleaching," Australian Dental Journal, vol. 53, 2008, pp. 128-132.

Manton, D. et al. "Remineralization of enamel subsurface lesions in situ by the use of three commercially available sugar-free gums.", International Journal of Paediatric Dentistry, vol. 18, 2008, pp. 284-290.

Manton, D. J. et al. "Remineralization of white spot lesions in situ by tooth mousse." Abstract 185—84$^{th}$ General Session of the IADR, Jun. 28-Jul. 1, 2006, Brisbane, Australia, Abstract.

Manton, D.J. "Promoting remineralization: using casein phosphopeptide-stabilized amorphous calcium (fluoride) phosphate. A chemical approach." EAPD, Amsterdam 8-II Jun. 2006, Abstract.

Manton, D.J. et al. "In situ remineralisation by sugar-free gums, one containing CPP-ACP." Abstract 0020—45$^{th}$ Annual Meeting of Australian/New Zealand Division of the IADR, Sep. 2005, pp. 25-28.

Mazzaoui, S.A. et al. "Incorporation of Casein Phosphopeptide-Amorphous Calcium Phosphate into a Glassionomer Cement." School of Dental Science, The University of Melbourne Research Reports (Jul. 2003) pp. 914-918.

Melkers, M.J. "Keeping focused on the finish line. Accomplishing goals with traditional and progressive technologies," Dentaltown, vol. 5—Issue 11, Nov. 2004, pp. 60, 62, 64 & 66.

Mellberg, J.R. et al. "Effect of soluble calcium on fluoride uptake by enamel from sodium monofluorophosphate" J Dent Res. 1982 vol. 61, No. 12, pp. 1394-1396.

MI Paste™ and MI Paste Plus™ [retrieved on Feb. 16, 2015] Retrieved from internet ,URL: http://web.archive.org/web/20140701070616/http://www.mipaste.com/about.php> published on Dec. 4, 2013 as per Wayback Machine whole document Wayback machine used to determine publication date, 2 pages.

MI Paste™ and MI Paste Plus™ [retrieved on Oct. 21, 2014] Retrieved from internet , URL: http://web.archive.org/web/20 I 31223044 I 14/http://www.gcamerica.com/products/preventive/MI _ Paste/> published on Dec. 23, 2013 as per Wayback Machine whole document Wayback machine used to determine publication date, 2 pages.

Mickenautsch, S. "An Introduction to Minimal Intervention Dentistry (MI).", Dental News, vol. XIV, No. IV, 2007, pp. 13-20.

Milnar, F.J. "Considering biomodification and remineralization techniques as adjuncts to vital tooth-bleaching regimens," Compendium vol. 28, No. 5, May 2007, pp. 234-240.

Minami et al., "Effects of Cheese and Milk Containing CPP-ACP on Enamel Remineralization", 2049—82$^{nd}$ General Session of the IADR, Mar. 2004, Honolulu, Hawaii. Abstract only.

Minimum Intervention: modernes Kariesmanagement—Weg vom chirurgichen, hin zum medizinischen Versorgungsansatz mit GC. IDS—31$^{st}$ International Dental Show, Cologne, Apr. 12-16, 2005 (Today—Independent Trade Show Daily—Saturday) English Abstract.

Mintel, "Mineralising Toothpaste," from Database GNPD, database accession No. 1368327 (Aug. 2010).

Misra, S. et al. "Early Childhood Caries—A Review," Dental Update, vol. 34, Dec. 2007, pp. 556-564. Abstract.

Miyazaki, M. et al. "Using ultrasound transmission velocity to analyze demineralization of tooth substrate." Abstract 94—52$^{nd}$ ORCA Congress, Jul. 2005, Indianapolis, USA I Caries Res vol. 39:319.

Morgan, M. V. et al. CPP-ACP gum slows progression and enhances regression of dental caries. Abstract 2445—84$^{th}$ General Session of the IADR, Jun. 28-Jul. 1, 2006, Brisbane, Australia. Abstract.

(56) References Cited

OTHER PUBLICATIONS

Morgan, MV et al. "A Clinical Trial Measuring White Spot Lesion Progression and Regression," Abstract 0112, Jul. 2008, Toronto, Canada.

Morgan, MV et al. "Clinical trial of tooth mousse on white spot lesions.", Cooperative research Centre for oral health science. Toronto, Briefing paper No. 2, 2008.

Morgan, MV et al. "The Anticariogenic Effect of Sugar-Free Gum Containing CPP-ACP Nanocomplexes on Approximal Caries Determined Using Digital Bitewing Radiography.", Caries Research, vol. 42, pp. 171-184, 2008.

Moule, C.A. et al. "Resin bonding using an all-etch or self-etch adhesive to enamel after carbamide peroxide and/or CPP-ACP treatment," Australian Dental Journal, vol. 52, No. 2, 2007, pp. 133-137.

Mount, GJ, "A new paradigm for operative dentistry,", Australian Dental Journal vol. 52, No. 4, 2007, pp. 264-270.

Murata et al., "Remineralization Power by Xylitol Chewing Gums", Abstract 2046—82nd General Session of the IADR, 2004, Honolulu, Hawaii. Abstract only.

Narayana, T. et al. "An in vitro study of wear prevention in dentine." Abstract 2424—84th General Session of the IADR, Jun. 28-Jul. 1, 2006, Brisbane, Australia.

Ng, H. et al. "Aesthetic management of severely fluorosed incisors in an adolescent female." Australian Dental Journal, vol. 52, No. 3, 2007, pp. 243-248.

O'Hehir, T "Caries- More than a filling," Hygientown.com, Jul./Aug. 2008, pp. 8-12.

Ono et al., "Complexes of Casein Phosphopeptide and Calcium Phosphate Prepared from Casein Micelles by Tryptic Digestion", Biosci. Biotech. Biochem. 58 (8), pp. 1376-1380, 1994.

Ono et al., "Preparation of Casein Phosphopeptides from Casein Micelles by Ultrafiltration", Biosci. Biotech. Biochem. 59 (3), pp. 510-511, 1995.

Oshiro, M. et al. "Effect of CPP-ACP paste on tooth mineralization: an FE-SEM study." Journal of oral Science, vol. 49, No. 2, 2007, pp. 115-120.

Pelletier et al. "Etude de la Réaction d'Hydrolyse de l'Anion P03F2—en Solution Aquese" Z. anorg. Allg. Chem. 581 (1990) 190-198.

Perdigao, J. et al. "Contemporary Trends and Techniques in Tooth Whitening: A Review", Practical Procedures & Aesthetic Dentistry, vo. 16, No. 3, 2004, pp. 185-192.

Perich et al., "Efficient Solution-Phase Synthesis of Multiple O-Phosphoseryl-Containing Peptides Related to Casein and Statherin", Int. J. Pept. Protein Res. (Aug. 1992), 40:2 pp. 81-88.

Perich et al., "The Use of Synthetic Phosphopeptides for Epitope Mapping of the ASI-Casein Phosphopeptide Segment 59-70", Bioorg. Med. Chern. Lett. (1992), 2: pp. 1153-1154.

Peschke, J.C. et al. "Nucleating Ability of Calcium Phosphate-Protein-Composites.", Abstract 2244, IADR Mar. 2007, New Orleans, USA.

Piekarz, C. et al. "An in vitro assessment of the role of Tooth Mousse in preventing wine erosion.", Australian Dental Journal, vol. 53, 2008, pp. 22-25.

Pietrzycka, K. "Chemical methods of treatment of dental caries: the action and application of CPP-ACP.", E-Dentico, vol. 2, No. 18, 2008, pp. 68-74. English Abstract.

Pitts, N.B. "Are we ready to move from operative to non-operative/preventive treatment of dental caries in clinical pmctice?", Caries Res, vol. 38, 2004, pp. 294-304.

Plate, U. et al. Investigation of the early mineralization on collagen in dentine of rat incisors by quantitative electron spectroscopic diffraction (ESD), Cell Tissue Res, vol. 278, 1994, pp. 543-547.

Poitevin et al., "Clinical Effectiveness of a CPP-ACP Crème for Tooth Hypersensitivity Treatment", EADR Istanbul, (Aug. 24-28, 2004), Abstract 0136.

Preventive agents; The Dental Advisor; 21(10):1-6 (Dec. 2004).

Products for the dental hygienist—Desensitizers. The Dental Advisor, vol. 23, No. 6, Jul./ Aug. 2006.

Quartarone, E. "Surface kinetic roughening caused by dental erosion: an atomic force microscopy study.", Journal of Applied physics, vol. 103, 2008, 104702, 1-6.

Rahiotis, C. et al. "Characterization of oral films formed in the presence of a CPP-ACP agent: An in situ study.", Journal of dentistry, vol. 36, 2008, pp. 272-280.

Rahiotis, C. et al. "Effect of a CPP-ACP agent on the demineralization and remineralization of dentine in vitro.", Journal of Dentistry, vol. 35, 2007, pp. 695-698.

Ramadas, "The oral care for children with malignancies"; Synopses; Synopses: The Newsletter of the Australian and New Zealand Society of Paediatric Dentistry, Winning 2003 Postgraduate Essay; 28:1-20 (Mar. 2004).

Ramalingam et al., "An in Vitro Investigation of the Effects of Casein Phosphopeptide-Stabilized Amorphous Calcium Phosphate (CPP-ACP) on Erosion of Human Dental Enamel by a Sports Drink", IADR, General Session, San Diego (2002), Abstract 2810.

Ramalingam et al., "Erosion of Human Dental Enamel by Sports Drinks", Synopses 27:16-19, (2003).

Ramalingam, L. et al. "Adding Caesin Phosphopetide-amorphous Calcium Phosphate to Sports Drinks to Eliminate In Vitro Erosion.", Pediatric Dentistry, vol. 27, No. 1, 61-67, 2005.

Ranjitkar, S. et al. Enamel wear prevention under conditions simulating bruxism and acid regurgitation. Abstract 2428—84th General Session of the IADR, Jun. 28-Jul. 1, 2006, Brisbane, Australia.

Ranjitkar, S. et al. "The Role of Tooth Mousse in preventing enamel wear," Poster 0375—session 39—42nd annual meeting of IADR-Continental European and Israeli Divisions, Sep. 26-29, 2007.

Ranjitkar, S. et al. "The role of tooth mousse in reducing erosive tooth wear," Abstract 2500, Jul. 2008, International Association for Dental Research, Toronto, Canada.

Rees, J. et al. "Pronamel and tooth mousse: An initial assessment of erosion prevention in vitro.", Journal of Dentistry, vol. 35, 2007, pp. 355-357.

Reeves et al., "Calcium Phosphate Sequestering Phosphopeptide from Casein." Science. vol. 128, p. 472 (1958).

Reich, E. "Das kleine gewisse Etwas zur Remineralisation", Zahnmedizin, vol. 95, No. 21, 2-9, 2005. English Abstract.

Reich, E. "Die Betreuung von Kariespatienten in der Praxis", Quintessenz, vol. 59, No. 12, 2008, pp. 1301-1307. English Abstract.

Reich, E. "Flüssiger Zahnschmelz." Dental Magazine. 2005. English Abstract.

Reich, E. "GC Tooth Mousse—Ein neuer Ansatz zur Remineralisation", Kongress: Wissenschaft und Praxis der Sanften Zahnheilkunde, Lindau am Bodensee, Mar. 3-4, 2006. English Abstract.

Reich, E. Dental Products Report Europe, Jan. 1, 2006.

Retention in Plaque and Remineralization of Enamel Lesions by Various Forms of Calcium in a Mouthrinse or Sugar-Free Chewing Gum. School of Dental Science, The University of Melbourne pp. 1-24.

Reynolds et al. "Additional Aids to the Reminersalisation of Tooth Structure," Preservation and Restoration of Tooth Structure Chapter 8, 111-118, 2005.

Reynolds et al., (1982) Phosphoprotein inhibition of Hydroxypatite dissolution. Calcif. Tissue Int. 34: S52-S56.

Reynolds et al., (1983) Effect of adsorbed protein on hydroxyapatite zeta potential and *Streptococcus mutans* adherence. Infection and Immunity 39(3): 1285-1290.

Reynolds et al., (1984) Effect of casein and whey-protein solutions on caries experience and feeding patterns of the rat. Arch. Oral. Biol. 29(11): 927-933.

Reynolds et al., (1987) Confectionary composition and rat caries. Caries Res. 21: 538-545.

Reynolds et al., (1987) Reduction of chocolate's cariogenicity by supplementation with sodium caseinate. Caries Res. 21: 445-451.

Reynolds et al., (1989) Protein dissimilation by human salivary-sediment bacteria. J. Dent.Res. 68:124-129.

Reynolds et al., "A Review of the Effect of Milk on Dental Caries", Aust. J. Dairy Tech., 34, pp. 175-179 (Dec. 1979).

Reynolds et al., "A Selective Precipitation Purification Procedure for Multiple Phosphoseryl-Containing Peptides and Methods for Their Identification", Anal. Biochem., (Mar. 1994), 217:2, pp. 277-284.

(56) References Cited

OTHER PUBLICATIONS

Reynolds et al., "Advances in Enamel Remineralization: Anticariogenic Casein Phosphopeptide-Amorphous Calcium Phosphate", J. Clin. Dent. (1999), X(2): pp. 86-88.
Reynolds et al., "Cariogenicity of a Confection Supplemented with Sodium Caseinate at a Palatable Level." Caries. Res. vol. 23. pp. 368-370 (1989).
Reynolds et al., "Effect of Milk on Caries Incidence and Bacterial Composition of Dental Plaque in the Rat", Arch Oral Biol. (1981) 26:5 pp. 445-451.
Reynolds et al., "Enamel Remineralization by Chewing Gum Containing Casein Phosphopeptide-Amorphous Calcium Phosphate", IADR, General Session, Chiba, Abstract 0489, (2001).
Reynolds et al., "Retention in Plaque and Remineralization of Enamel Lesions by Various Forms of Calcium in a Mouthrinse or Sugar-free Chewing Gum," J Dent Res 82(3): 206-211, 2003.
Reynolds, (1987) The prevention of sub-surface demineralization of bovine enamel and change in plaque composition by casein in an intra-oral model. J. Dental Res. 66(6): 1120-1127.
Reynolds, "Anticariogenic Casein Phosphopeptides", Prot. Peptide Lett. (1999), pp. 295-303.
Reynolds, "Caries Prevention and Oral Health", Health Aspects of Dairy Products/Caries Prevention and Oral Health, 2002. pp. 1306-1313.
Reynolds, "Dairy Components in Oral Health", Aust. J. Dairy Tech. 58: pp. 79-81, (2003).
Reynolds, "The Role of Phosphopeptides in Caries Prevention", Dental Perspectives (1999), 3, pp. 6-7.
Reynolds, 1998, "Anticariogenic complexes of amorphous calcium phosphate stabilized by casein phosphopeptides: A review." Journal of Special Care in Dentistry, vol. 18:1, pp. 8-16.
Reynolds, E. "Calcium phosphate-based remineralizatron systems: scientific evidence?" Australian Dental Journal, vol. 53, 2008, pp. 268-273.
Reynolds, E. C. et al. "Improved plaque uptake and enamel remineralization by fluoride with CPP-ACP." Abstract 2538—84$^{th}$ General Session of the IADR, Jun. 28-Jul. 1, 2006, Brisbane, Australia.
Reynolds, E. C., "Remineralization of Enamel Subsurface Lesions by Casein Phosphopeptide-stabilized Calcium Phosphate Solutions," *J Dent Res.*, 76:9 1587-1595 (1997).
Reynolds, E.C. "Dairy Products and Dental Health," *Proceedings of the Nutrition Society of Australia* pp. 95-102 (1995).
Reynolds, EC et al. "Fluoride and casein phosphopeptide-amorphous calcium phosphate.", J Dent Res vol. 87, No. 4, 2008, pp. 344-348.
Reynolds, EC. "Remineralization of early enamel caries by anti-cariogenic casein phosphopeptide-amorphous calcium phosphate nanocomplexes." Dental Practice Nov./Dec. 2001, 3 pages.
Reynolds, et al., "Anticariogenicity of Calcium Phosphate Complexes of Tryptic Casein Phosphopeptides in the Rat," *J Dent Res*, 74(6): 1272-1279 (1995).
Roberts MJ et al. "Remineralisation of fluorotic enamel lesions by casein phosphopeptide—amorphous calcium 17odems17te17phates (CPP-ACFP) solution." IADR,ANZ division, Abstract 54, 2000.
Roberts, "Role of Models in Assessing New Agents for Caries Prevention-Non-Fluoride Systems", Adv. Dent. Res. (Nov. 1995), 9(3), pp. 304-311; discussion 312-314.
Robinson et al. "Effect of Surface Zone Deproteinisation on the Access of Mineral Ions into Subsurface Carious Lesions of Human Enamel", Caries Res 1990; 24:226-230.
Rose, "Binding Characteristics of *Streptococcus mutans* for Calcium and Casein Phosphopeptide", Caries. Res. (2000), 34, pp. 427-431.
Rose, "Effects of an Anticariogenic Casein Phosphopeptide on Calcium Diffusion in Streptococcal Model Dental Plaques", Arch Oral Bioi, vol. 45, Issue 7, (2000) pp. 569-575.
Rosen et al., "Effect of Cheese, With and Without Sucrose, On Dental Caries and Recovery of *Streptococcus mutans* in Rats", J. Dent. Res. 63: pp. 894-896, (1984).
Rozwadowska, E. "Children and private dentistry." Private Dentistry, May 2006, pp. 109-113.
RT Basting, "The Effect of 10% Carbamide Peroxide Bleaching Material on Microhardness of Sound and Demineralized Enamel and Dentin In Situ" Clinical Research, Operative Dentistry, 2001, 26, pp. 531-529.
Sakaguchi, Y. et al. "Preventing acid induced enamel demineralization using CPP-ACP containing paste." Abstract 2055—IADR, Mar. 2005, Baltimore, Maryland, USA.
Sakaguchi, Y. et al. "Remineralization potential of CPP-ACP and its synergy with fluoride," Abstract 191—84$^{th}$ General Session of the IADR, Jun. 28-Jul. 1, 2006, Brisbane, Australia.
Sato et al. "Caries prevention Potential of a Tooth-coating Material Containing Casein Phospho peptide—Amorphous Calcium Phosphate (CPP-ACP)," IADR, General session, Goteborg, 2003, Abstract 1007.
Schüpbach et al., "Incorporation of Caseinoglycomacropeptide and Caseinophosphopeptide into the Salivary Pellicle Inhibits Adherence of Mutans Streptococci", J. Dent. Res, vol. 75, pp. 1779-1788, (1996).
Schweigert, BS et al. "Dental caries in the cotton rat. VI. The effect of the amount of protein, fat and carbohydrate in the diet on the incidence and extent of carious lesions". J. Nutr., vol. 31, 1946, pp. 439-447.
Shaw JH "Effects of dietary composition on tooth decay in the albino rat." J. Nutr. 41, 1950, pp. 13-23.
Sheharyar, S. et al. "Efficacy of MI Paste For Sensitivity Associated With Vital Bleaching," Abstract 2041, IADR Mar. 2007, New Orleans, USA.
Shen et al., "Enamel remineralization by a mouthrinse containing casein phosphopeptide-amorphous calcium phosphate and fluoride in an in situ model"; Australian Dental Journal ADRF; Special Research Supplement, 49(4):S19 (2004).
Shen et al., "Remineralization of Enamel Subsurface Lesions by Sugar-free Chewing Gum Containing Casein Phosphopeptide-Amorphous Calcium Phosphate," J Dent Res 80(12):2066-2070, 2001.
Shen, P. et at. "Remineralization by a mouthrinse containing CPP-ACP at pH 5.5.", Abstract 189—84$^{th}$ General Session of the IADR, Jun. 28-Jul. 1, 2006, Brisbane, Australia.
Silva et al., "Effects of Water-soluble Components of Cheese on Experimental Caries in Humans," J Dent Res 66(1):38-41, Jan. 1987.
Silva, Margarita et al. "Fluoride content of infant formulae in Australia." Australian Dental Journal 1996:41:1. pp. 37-42.
Slomiany, B. et al. "Salivary Mucins in Oral Mucosal Defense", Gen. Pharmac., vol. 27, No. 5, 1996, pp. 761-771.
Smith, S. "Ultramorphological evaluation of dentin after treatment with different desensitizing agents," Abstract 0941, IADR 2007, New Orleans, USA.
Smolenski, D. et al. "MI Paste and Fluoride for Caries Prevention In-Vitro.", Abstract 0505, IADR 2007, New Orleans, USA.
Steinberg, S. "A modern paradigm for caries management, Part 1: Diagnosis and Treatment." Dentistry Today, Feb. 2007.
Steinberg, S. "A modern paradigm for caries management, Part 2: A practical protocol." Dentistry Today, Jun. 2007.
Stößer, L. "Kariesprotektive Eigenschaften des durch Caseinphosphopeptid stabilisierten amorphen Calciumphosphat-Nanokomplexes (CPP-ACP)," Deutsche Zahniirztliche Zeitschrift, vol. 62 (9), pp. 579-588 (2007).
Sudjalim, T.R. et al. Prevention of demineralization around orthodontic brackets in vitro. American Journal of Orthodontics and Dentofacial Orthopedics., 2007, 131, 6, pp. 705.e1-705.E9.
Sudjalim, T.R. et al. "Prevention of white spot lesions in orthodontic practice: a contemporary review.", Australian Dental Journal, vol. 51, No. 4, 2006, pp. 284-289.
Sukasaem, H. et al. "Effect of CPP-ACP on hardness of enamel eroded by Cola-drink." Abstract 1673—84$^{th}$ General Session of the IADR, Jun. 28-Jul. 1, 2006, Brisbane, Australia.
Supplementary European Search Report issued on Dec. 13, 2016 in application No. EP 14 83 0019.

(56) References Cited

OTHER PUBLICATIONS

Takamizawa, T et al. "Determination of demineralization of tooth substrate by use of an ultrasonic device." Japan J Conserv Dent Jun vol. 47 Spring Issue 24—Abstract B-4, 2004.
Talbo et al., "MALDI-PSD-MS Analysis of the Phosphorylation Sites of Caseinomacropeptide", Peptides (Jul. 2001) 22:7, pp. 1093-1098.
Tantbirojn, D. et al. "Changes in surface hardness of enamel by a cola drink and CPP-ACP paste," Journal of Dentistry, vol. 36, 2008, pp. 74-79.
Tay et al. "Assessing the Effect of a Desensitizing Agent Used Before In-office Tooth Bleaching," The Journal of the American Dental Association, vol. 140, Issue 10, (Oct. 2009); pp. 1245-1251.
Ten Cate, Jacob M. "Current concepts on the theories of the mechanism of action offluoride." Acta Odontol, Scand 57 (1999), 325-329.
Theerapiboon, U. et al. "Remineralization of artificial caries by CPP-ACP paste.", Abstract 3274, Jul. 2008, International Association for Dental Research, Toronto, Canada.
Trajtenberg, C.P. et al. "CPP-ACP Paste with Fluoride: In Vitro Root Surface Caries Formation," Abstract 0500, IADR 2007 New Orleans, USA.
Translation of Japanese Office Action from Application No. 2002-590925, Nov. 18, 2008.
Translation of Russian Office Action from Application No. 2007123603, May 26, 2009.
Turssi, C.P. et al. "Progression of erosion following use of calcium and phosphorus compounds.", Abstract 2499, Jul. 2008, International Association for Dental Research, Toronto, Canada.
Ung, M. et al. "Investigation of the binding of casein phosphopeptides to the major enamel pellicle proteins.", Australian Dental Journal ADRF Special Research Supplement vol. 49, No. 4, S19-S20, 2004.
VB Haywood, "History, safety, and effectiveness of current bleaching techniques and applications of the nightguard vital bleaching technique" Quintessence Int. Jul. 1992; 23(7): 471-88. (Year: 1992).
Vlacic et al., "Combined CPP-ACP and photoactivated disinfection (PAD) therapy in arresting root surface caries: a case report"; British Dental Journal; 203(8):457-459 (2007).
Walker et al., "Consumption of milk with added casein phosphopeptide-amorphous calcium phosphate remineralizes enamel subsurface lesions in situ," Australian Dental Journal, vol. 54, No. 3, pp. 245-249, Sep. 2009.
Walker, Glen et al. "Increased remineralization of tooth enamel by milk containing added casein phosphopeptide amorphous calcium phosphate." Journal of Dairy Research (2006) 73, pp. 74-78.
Walsh, "Tooth Mousse Information," GC Tooth Mousse Portfolio 2nd Edition, Mar. 2005.
Walsh, L. "Application of the System for Total Environmental Management (STEM) to demineralization, dental erosion and tooth wear," Australasian Dental Practice, Jan.-Feb. 2008, pp. 52-58.
Walsh, L.J. "The effects of GC Tooth Mousse on cervical dentinal sensitivity: a controlled clinical trial", International Dentistry SA—Australasian Edition vol. 12, No. 1, 4-12, 2010.
Walsh, L.J. et al. "Effect of CPP-ACP versus potassium nitrate on cervical dentinal hypersensitivity," Abstract 947—84th General Session of the IADR, Jun. 28-Jul. 1, 2006, Brisbane, Australia.
Weiss, Dr. V. "Kariesprophylaxe in der kinderzahnnärztlichen Praxis", ZWP, Oct. 2005, 18 pp. 76-79. English Abstract.
Westerman, G. et al. "Argon Laser and Remineralizing Paste Effect on Root Surface Caries," Abstract 0018, IADR Mar. 2007, New Orleans, USA.
White, "Use of Synthetic Polymer Gels for Artificial Carious Lesion Preparation" Caries Research 21, 1987, pp. 228-242. Abstract Only.
Wilfershausen, B. et al. "In-Vitro-Studie Zur Überprüfung einermöglichen Remeralisation durch caesinphosphopetidhaltige Calciumphosphat-komplexe (CPP ACP).", Deutsche Zahnarztiche Zeitschrift, vol. 63, No. 2, 2008, pp. 134-139. English Abstract.
Wilkiel, et al., "Hydroxyapatite Mineralization and Demineralization in the Presence of Synthetic Phosphorylated Pentapeptides," Archives of Oral Biology, 39:8, 715-721 (1994).

William, V. et al. "Molar Incisor Hypomineralization: Review and Recommendations for Clinical Management", Pediatric Dentistry, vol. 28, No. 3, 224-232, 2006.
Wong, L, et al. "Plaque microcosm biofilm mineralization by CPP-ACP and calcium-phosphatemonofluorophosphate-urea mineralizing solution." Abstract 1269—84th General Session of the IADR, Jun. 28-Jul. 1, 2006, Brisbane, Australia.
Wong, R. et al. Incorporation of casein phosphopeptide-amorphous calcium phosphate into a temporary cement. Abstract 0653—84th General Session of the IADR, Jun. 28-Jul. 1, 2006, Brisbane, Australia.
Wright, S. et al. "Artificial Caries Inhibited with MI Paste and Two Restorative Materials," Abstract 2777, IADR 2007, New Orleans, USA.
Xie, Q. et al. "Remineralization Effects of CPP-ACP and Proanthocyanidin on Artificial Root Caries," Abstract 0512, IADR 2007, New Orleans, USA.
Yamaguchi, K. et al. "Effect of CPP-ACP paste on mechanical properties of bovine enamel as determined by an ultrasonic device," Journal of Dentistry, vol. 34, 2006, pp. 230-236.
Yamaguchi, K. et al. "Ultrasonic determination of the effect of casein phosphopeptide-amorphous calcium phosphate paste on the demineralization of bovine dentin," Caries Res, vol. 41, 2007, pp. 204-207.
Zero, "Dentifrices, mouthwashes, and remineralization/caries arrestment strategies," BMC Oral Health, vol. 6 (Suppl I)S9, pp. 1-13 (Jul. 2010).
Zero, DT "In situ caries models." Adv Dent Res vol. 9(3), 1995, pp. 214-230.
Zhang, L, et al. "Experimental study of phosphopeptide in promoting tooth remineralisation." Chinese J Dent Res., vol. 3(1), May 2000, pp. 27-30.
Zhao et al. "The remineralization for enamel lesions by casein phosphopeptide-amorphous calcium fluoride 21odems21te in vitro." Zhonghua Kou Qiang Yi Kxue Za Zhi. vol. 36. No. 6. 2001. pp. 421-423, with English translation.
Colgate, Fluoride Conversions, Colgate professional.com (Feb. 2013).
Mitthra et al., "Mineral Loss before and after .Bleaching and Mineral Uptake on Application of Remineralizing Agent", Indian Journal of Multidisciplinary Dentistry and Endodontics, vol. 1, No. 1, Jan. 2010.
De Oliveira et al. "In situ effect of a CPP-ACP chewing gum on enamel erosion associated or not with abrasion"; Clin Oral Investig. 21:339-346 (Mar. 2016).
Farooq et al., "A review of novel dental caries preventative material: Casein phosphoepetide-amorphous calcium phosphate (CPP-ACP) complex," King Saud University Journal of Dental Sciences (2013) 4, 4751.
CPP-ACP_and_gingivitis_Google_Scholar_12-12-21.pdf (2021).
I. L. C. Chapple et al., "Primary prevention of periodontitis: managing gingivitis," Journal of Clinical Periodontology, vol. 42 (Suppl. 16): S71-S76 (2015).
L. Walsh, "Clinical Aspects of Salivary Biology for the Dental Clinician," International Dentistry South Africa (Australasian Edition) vol. 9, No. 4, pp. 22-41 (2007).
Google scholar search_9-21-2020_GC Tooth Mousse periodontitis (2020).
Google scholar serach_9-21-2020_oral dysbiosis (2020).
Google Search_9/22/2020_removing supragingival bacteria with brushing (2020).
Kilian et al., "The oral microbiome-an update for oral healthcare professionals," British Dental Journal, vol. 221, No. 10, pp. 657-666 (Nov. 2016).
Martinez-Pablon et al., "Comparison of the Effect of Two Sugar-Substrate Chewing Gums on Different Caries- and Gingivitis-Related Variables: a Double-Blind, Randomized, Controlled Clinical Trial," Clinical Oral Investigations (2014) 18: 589-598.
Sakr et al., "The Effect of Recaldent (CPP-ACP) on the most putative bacteria in caries and chronic gingivitis," Ain Shams Dental Journal, vol. X, No. 2 pp. 211-219 (Jun. 2007).

(56) References Cited

OTHER PUBLICATIONS

Zanatta et al., "Supragingival Plaque Removal with and without Dentifrice: A Randomized Controlled Clinical Trial," Braz Dent J, vol. 23, No. 3, pp. 235-240 (2012).
Google scholar search_6-16-21 dysbiosis recaldent (2021).
Google scholar search_6-16-21_ACP phosphopeptide and oral microbiome (2021).
Llena et al., "Anticariogenicity of Casein Phosphopeptide-amorphous Calcium Phosphate: A Review of the Literature," Journal of Contemporary Dental Practice, vol. 10, No. 3 pp. 1-9 (May 2009).
Walsh, L., "Clinical applications of Recaldent products: which ones to use where," Australasian Dental Practice May/Jun. 2007, pp. 144-146 (2007).
Walsh, "Topical CPP-ACP crèmes beyond caries prevention," International Dentistry, African Edition, vol. 4, No. 5 pp. 26-32 (2014).
Munjal, D. et al., "Assessment of White Spot Lesions and In-Vivo Evaluation of the Effect of CPP-ACP on White Spot Lesions in Permanent Molars of Children", Journal of Clinical and Diagnostic Research, vol. No. 10, Issue No. 5, May 2016, pp. 149-154.
Chen, Y. et al. "Research progress of complex of casein phosphopeptide and amorphous calcium phosphate in oral therapy", Chin. J. Aesth. Med., vol. 23, No. 8, pp. 681-683 (2014).
U.S. Appl. No. 18/052,390, filed Nov. 3, 2022, Reynolds, Eric Charles.
U.S. Appl. No. 18/210,381, filed Jun. 15, 2023, Reynolds, Eric Charles.
U.S. Appl. No. 18/214,964, filed Jun. 27, 2023, Reynolds, Eric Charles.
Ajaj et al., "Effect of different acid etchants on the remineralization process of white-spot lesions: An in vitro study.", American Journal of Dentistry, Feb. 2020; pp. 43-47.
Hsu C.-Y.S. et al., "Laser-Matrix-Fluoride Effects on Enamel Demineralization", Journal of Dental Research, Sep. 2001; vol. 80, No. 9, pp. 1797-1801.
Huang et al., "Remineralisation Effect of CPP-ACP and Diode Laser Stabilised by Case on the Initial Enamel caries of Primary Teeth", Progress in Modern Biomedicine, Jan. 2019; 19(2): 279.
Kshirsagar et al., "Comparative assessment of bond strengths of affected dentin, using two different remineralizing solutions with or without lasers: Results of an in vitro pilot study", SRM Journal of Research in Dental Sciences, Jan. 2015; vol. 6, No. 2.
L.J. Walsh "Clinical applications of Recaldent products: which ones to use where," Australasian Dental Practice, May/Jun. 2007, 144-146. (Year: 2007).
Sakr, A. K., ELkarargy, A. A. M., & Sherif, M. M. (2007). The Effect of Recaldent (CPP-ACP) on the most putative bacteria in caries and chronic gingivitis. Ain Shams Dental Journal, 211-219. (Year: 2007).
Verguard et al., "Mineral-binding milk proteins and peptides; occurrence, biochyemical and technological characteristics", British Journal of Nutrition, Nov. 2000; 84: Suppl. 1, S91-S98.
White, A return to stannous fluoride dentrifices, Journal of clinical dentistry, Feb. 1995; Spec No. 29-36.

\* cited by examiner

Treatment: Double Distilled Water (DDW)

Treatment: Sn/CPP molar ratio 1.6:1

Treatment: Sn/CPP molar ratio 1.6:1

Treatment: Sn/CPP molar ratio 1.6:1

Treatment: Sn/CPP molar ratio 4:1

Treatment: Sn/CPP molar ratio 8.6:1.

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Phosphopeptides
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(10)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 1

Gln Met Glu Ala Glu Ser Ile Ser Ser Ser Glu Glu Ile Val Pro Asn
1               5                   10                  15

Ser Val Glu Gln Lys
            20

<210> SEQ ID NO 2
<211> LENGTH: 25
<212> TYPE: PRT
<213> ORGANISM: Artificial Sequence
<220> FEATURE:
<223> OTHER INFORMATION: Phosphopeptides
```

```
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (17)..(19)
<223> OTHER INFORMATION: PHOSPHORYLATION

<400> SEQUENCE: 2

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

<210> SEQ ID NO 3
<211> LENGTH: 25
<212> TYPE: PRT
<213> ORGANISM: Artificial Sequence
<220> FEATURE:
<223> OTHER INFORMATION: Phosphopeptides
<220> FEATURE:
<221> NAME/KEY: MOD_RES
<222> LOCATION: (11)..(13)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 3

Asn Ala Asn Glu Glu Glu Tyr Ser Ile Gly Ser Ser Ser Glu Glu Ser
1               5                   10                  15

Ala Glu Val Ala Thr Glu Glu Val Lys
            20                  25

<210> SEQ ID NO 4
<211> LENGTH: 21
<212> TYPE: PRT
<213> ORGANISM: Artificial Sequence
<220> FEATURE:
<223> OTHER INFORMATION: Phosphopeptides
<220> FEATURE:
<221> NAME/KEY: MOD_RES
<222> LOCATION: (8)..(10)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 4

Lys Asn Thr Met Glu His Val Ser Ser Ser Glu Glu Ser Ile Ile Ser
1               5                   10                  15

Gln Glu Thr Tyr Lys
            20
```

COMPLEXES FOR TREATING SENSITIVITY

CROSS REFERENCE TO RELATED APPLICATIONS

This application is the U.S. National Stage of International Application No. PCT/AU2018/050230, filed Mar. 14, 2018, which claims priority from Australian provisional Application No. 2017900892, filed Mar. 14, 2017, the entire contents of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Feb. 3, 2020 and is named 040268-0223-Sequence-listing-.TXT and is 2,136 bytes in size.

FIELD OF THE INVENTION

The present invention relates to improved phosphopeptide stabilised amorphous calcium phosphate and/or amorphous calcium fluoride phosphate complexes and compositions containing those complexes. Methods of making the complexes of the invention and of treating or preventing dental sensitivity are also provided.

BACKGROUND OF THE INVENTION

The three mineralized components of teeth are enamel, cementum and dentine. In human teeth, enamel covers the crown dentine whereas cementum covers the root dentine. The dentine encloses the pulp of the tooth which provides the dentine with vascular and neural support. Unlike enamel and cementum, the dentine is transversed by a network of tubular structures, termed dentinal tubules. These tubules are shielded by the enamel (crown) and the cementum (root), which form a protective layer of the pulp against external physical and chemical influences, like temperature changes and acids, and prevent affection of the nerve protrusions and dentin hypersensitivity. The diameter of the dentinal tubules which protrude into the dentin layer and are open to the dental surface varies between 1 and 2.5 µm.

The tubule walls in dentine are comprised of the calcified matrix of the dentine and the tubule space is filled with fluid (dentinal fluid) derived from pulp tissue fluid and serum. Because of their rigid walls, the fluid that fills the narrow dentinal tubules enables cold, tactile, evaporative and osmotic stimuli to be transmitted through the dentine to the pulp in the form of fluid movement. This movement of dentinal fluid is sensed as sharp pain of short duration. This pain is elicited when the odontoblasts that protrude into the pulpal ends of the tubules are disturbed and as a result, the mechano-receptors of the pulpal nerve fibers attached thereto are stimulated. The neural response is usually referred to as dentinal pain and the involved dentine as hypersensitive dentine.

Dentinal hypersensitivity results when protective enamel or cementum covering dentine is lost. Cementum is typically easier to breach than enamel, because cementum is thinner and more easily eroded by acids. However, breach of cementum cannot happen until there is gingival recession and exposure of the root surface to the oral environment. Individuals with breached cementum and suffering with dentinal hypersensitivity often experience pain when the exposed area of the tooth comes into contact with cold air, hot and cold liquids, foods that are sweet or acidic, or is touched with a metal object. Patients suffering from tooth hypersensitivity have larger number of open dentinal tubules and/or tubules with a larger in diameter than normal.

WO2015/095932 describes complexes that have certain beneficial properties. The present invention exhibits significant advantages over those complexes.

There is a need for compositions and methods for minimising exposure of dentinal tubules to treat and/or prevent dentinal sensitivity.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the invention provides a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP.

Preferably, the stannous ion content of the complex is between about 1 mole of stannous per mole of PP and about 2 moles of stannous per mole of PP. The stannous ion content of the complex may be about 1 mole of stannous per mole of PP or about 2 moles of stannous per mole of PP. Most preferably, the stannous ion content of the complex is about 1.6 moles of stannous per mole of PP.

In other aspect, the present invention provides a composition comprising a stannous-associated phosphopeptide (PP) stabilized amorphous calcium phosphate (ACP) or amorphous calcium fluoride phosphate (ACFP) complex of the invention.

In another aspect, the present invention provides a composition comprising a phosphopeptide (PP) stabilized amorphous calcium phosphate (ACP) and/or amorphous calcium fluoride phosphate (ACFP) complex, and a stannous compound, wherein the composition has a stannous ion content of equal to, or greater than, 1 mole of stannous per mole of PP but less than 4 moles of stannous per mole of PP.

Preferably, the stannous ion content of the composition is between about 1 mole of stannous per mole of PP and about 2 moles of stannous per mole of PP. The stannous ion content of the composition may be about 1 mole of stannous per mole of PP or about 2 moles of stannous per mole of PP. Most preferably, the stannous ion content of the composition is about 1.6 moles of stannous per mole of PP.

Preferably, the composition further includes a pharmaceutically acceptable carrier, diluent or excipient.

In another aspect, the present invention also provides a method for treating or preventing dentinal sensitivity in an individual in need thereof comprising administering a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP, thereby treating or preventing dentinal hypersensitivity in the individual.

In another aspect, the present invention also provides a method for treating or preventing dentinal sensitivity in an individual in need thereof comprising administering a composition comprising a phosphopeptide (PP) stabilized amorphous calcium phosphate (ACP) and/or amorphous calcium fluoride phosphate (ACFP) complex, and a stannous compound, wherein the composition has a stannous ion content of equal to, or greater than, 1 mole of stannous per mole of PP but less than 4 moles of stannous per mole of PP, thereby treating or preventing dentinal hypersensitivity in an individual.

Preferably, the dentinal sensitivity is dentinal hypersensitivity.

Preferably, the method further comprises the step of identifying an individual in need of treatment. For example, the invention includes, in addition to the steps of any method described herein, a step of identifying a subject suffering dentinal sensitivity, specifically hypersensitivity.

In another aspect, the present invention provides a method for occluding exposed dentinal tubules in an individual, the method comprising administering:

a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP; or a composition comprising a phosphopeptide (PP) stabilized amorphous calcium phosphate (ACP) and/or amorphous calcium fluoride phosphate (ACFP) complex, and a stannous compound, wherein the composition has a stannous ion content of equal to, or greater than, 1 mole of stannous per mole of PP but less than 4 moles of stannous per mole of PP, thereby occluding exposed dentinal tubules in an individual.

In another aspect, the present invention provides a method for forming a layer over exposed dentinal tubules in an individual, the method comprising administering:

a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP; or a composition comprising a phosphopeptide (PP) stabilized amorphous calcium phosphate (ACP) and/or amorphous calcium fluoride phosphate (ACFP) complex, and a stannous compound, wherein the composition has a stannous ion content of equal to, or greater than, 1 mole of stannous per mole of PP but less than 4 moles of stannous per mole of PP, thereby forming a layer over exposed dentinal tubules in an individual.

Preferably, the method of occluding exposed dentinal tubules or forming a layer over exposed dentinal tubules further comprises the step of identifying exposed dentinal tubules in an individual.

In another aspect, the present invention provides the use of:

a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP; or a composition comprising a phosphopeptide (PP) stabilized amorphous calcium phosphate (ACP) and/or amorphous calcium fluoride phosphate (ACFP) complex, and a stannous compound, wherein the composition has a stannous ion content of equal to, or greater than, 1 mole of stannous per mole of PP but less than 4 moles of stannous per mole of PP, in the manufacture of a medicament for the treatment or prevention of dentinal sensitivity. Preferably, the dentinal sensitivity is dentinal hypersensitivity.

In another aspect, the present invention provides, a stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP; or a composition comprising a phosphopeptide (PP) stabilized amorphous calcium phosphate (ACP) and/or amorphous calcium fluoride phosphate (ACFP) complex, and a stannous compound, wherein the composition has a stannous ion content of equal to, or greater than, 1 mole of stannous per mole of PP, but less than 4 moles of stannous per mole of PP, for use in the treatment or prevention of dentinal sensitivity. Preferably, the dentinal sensitivity is dentinal hypersensitivity.

In any aspect of the invention described herein, the stannous ion content is between about 1 mole of stannous per mole of PP and about 2 moles of stannous per mole of PP. The stannous ion content may be about 1 mole of stannous per mole of PP or about 2 moles of stannous per mole of PP. Most preferably, the stannous ion content is about 1.6 moles of stannous per mole of PP.

In any aspect of the invention, a complex of the invention, or composition of the invention, is administered to the oral cavity. Alternatively, administration may be directly to an oral site in need of treatment, for example a site that has exposed dentine. In either case, administration results in contact of the complex or composition to an oral site in need of treatment, such as exposed dentine.

In any aspect of the invention, the phosphopeptide is a casein phosphopeptide.

In one embodiment, the stannous-associated phosphopeptide (PP) stabilized amorphous calcium phosphate (ACP) complex consists essentially of, or consists of, phosphopeptides, stannous, calcium, phosphate and hydroxide ions and water.

In one embodiment, the stannous-associated phosphopeptide (PP) stabilized amorphous calcium phosphate (ACFP) complex consists essentially of, or consists of, phosphopeptides, stannous, calcium, phosphate, fluoride and hydroxide ions and water.

In any aspect or embodiments as described herein, the stannous-associated phosphopeptide (PP) stabilized ACP or ACFP complex may be in a formulation with additional calcium phosphate. Typically, the formulation includes a stannous-associated phosphopeptide (PP) stabilized ACP or ACFP complex together with at least an equal amount by weight of calcium phosphate.

In any aspect or embodiment of the invention described herein, a composition of the invention, or a stannous-associated PP stabilized ACP or ACFP complex of the invention, may be applied to the mouth, tooth or exposed dentine by the subject in need of treatment or by a dental health care professional.

A stannous-associated phosphopeptide (PP) stabilized amorphous calcium phosphate (ACP) or amorphous calcium fluoride phosphate (ACFP) complex of the invention, or composition of the invention, may be contacted with the dental surface for a period of about 1 to 60 minutes, for about 1 to 30 minutes, for about 10 to 60 minutes, for about 10 to 30 minutes, for about 20 to 60 minutes, or for about 20 to 30 minutes. Preferably, the complex or composition is contacted with the dental surface for about 20 minutes.

In another aspect, the present invention provides a method of mineralizing a dental surface or sub-surface comprising contacting the dental surface or subsurface with a stannous-associated phosphopeptide (PP) stabilized amorphous calcium phosphate (ACP) or amorphous calcium fluoride phosphate (ACFP) complex of the invention, or composition of the invention, thereby mineralizing the dental surface or subsurface.

In a preferred embodiment of the invention, the stannous-associated phosphopeptide stabilised amorphous calcium phosphate (ACP) or amorphous calcium fluoride phosphate (ACFP) complex in the composition has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

In another preferred embodiment of the invention, the calcium ion content of the stabilised ACP or ACFP complex, or complex in a composition, is greater than 30 moles of calcium per mole of PP. Preferably, the calcium ion content of the stabilised ACP or ACFP complex is in the range of about 30 to 100 moles of calcium per mole of PP. More preferably, the calcium ion content is in the range of about 30 to about 50 moles of calcium per mole of PP.

The invention also relates to a kit for the treatment or prevention of dentinal hypersensitivity comprising:
(a) a composition of the invention, or
(b) a stannous-associated phosphopeptide stabilized ACP or ACFP complex of the invention.

Preferably, the stannous-associated phosphopeptide stabilized ACP or ACFP complex is in a pharmaceutically acceptable carrier. Desirably, the kit further includes instructions for their use for treating or preventing dentinal hypersensitivity in an individual in need of such treatment. In one embodiment, the composition and the complex are present in suitable amounts for treatment of an individual.

The composition or kit of the invention may further include a source of fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
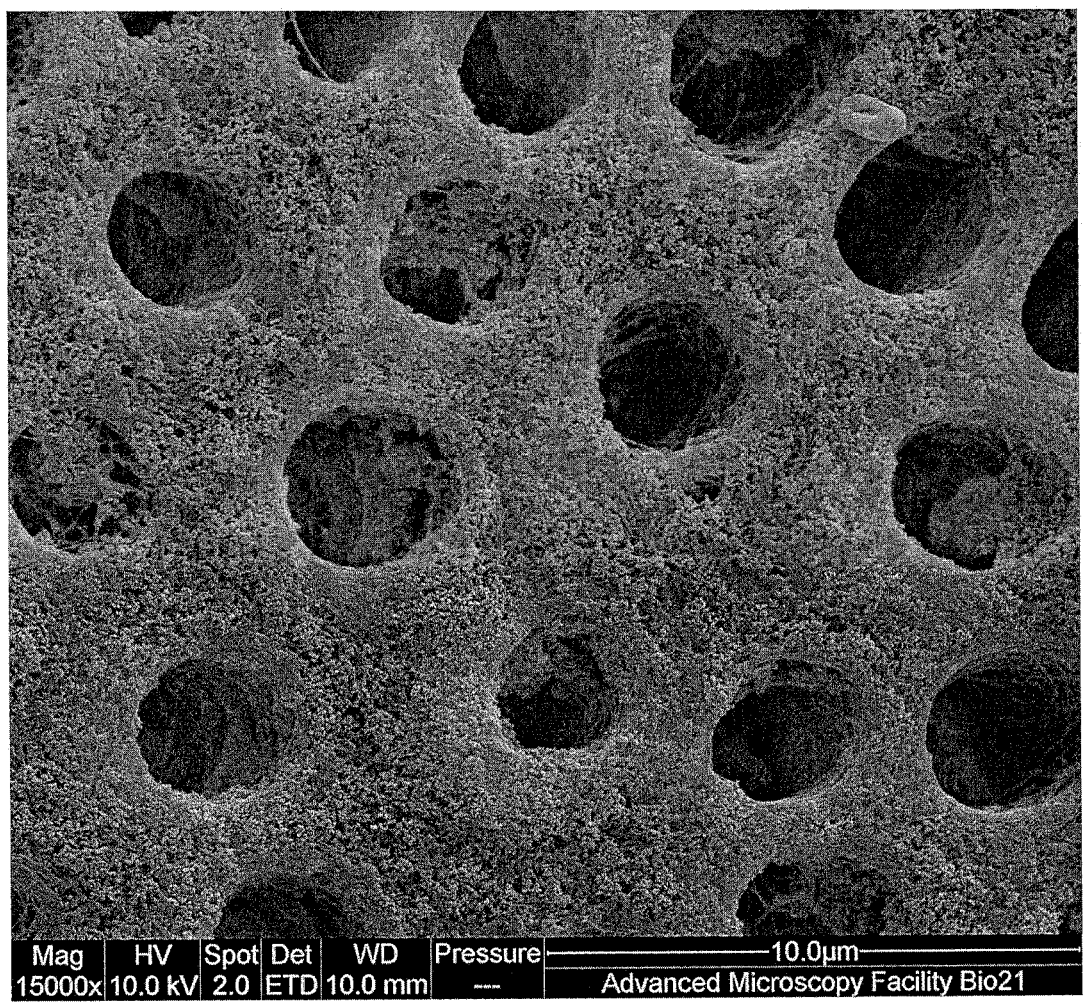
FIG. 1. Scanning electron microscopy (SEM) of patients' dentine tubules treated with distilled, deionised water (DDW). Magnification 15,000× and 10 μM scale shown. Exposed dentine tubules are clearly visible with no occlusion.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include" can be used interchangeably.

The present invention is based on the surprising finding that stannous-associated phosphopeptide (PP) stabilized amorphous calcium phosphate (ACP) or amorphous calcium fluoride phosphate (ACFP) complex having a stannous ion content of equal to, or greater than, 1 mole of stannous per mole of PP but less than 4 moles of stannous per mole of PP can form self-assembled nanofilaments which can occlude dentinal tubules. Specifically, the self-assembled nanofilaments form to such an extent that they span the entirely opening of dentinal tubules while forming network of nanofilaments across the dentine surface. This does not occur with a stannous ion content of greater than 4 moles per mole of phosphopeptide.

Without being bound by any theory or mode of action, it is believed that the stannous ions and phosphopeptides interact with the dentine surface to result in a unique pattern of surface coverage that displays a self-assembled network of nanofilaments across the dentine surface occluding the tubules. These nanofilaments are thought to be stannous cross-linked phosphopeptide which have released their cargo of calcium, phosphate and fluoride ions at the surface upon nanofilament formation. The results shown herein indicate that the molar ratio of equal to, or greater than, 1 mole but less than 4 moles of stannous to phosphopeptide is critical for the formation of cross-linked nanofilaments and therefore enhanced reduction in dentinal hypersensitivity.

The stannous containing compound, or stannous compound, can be any soluble stannous containing compound suitable for oral use. Preferably, stannous containing compound is a stannous salt. The stannous salt may contain fluoride. A stannous salt includes, but not limited to, stannous fluoride, stannous chloride, potassium stannous fluoride, sodium stannous fluorozirconate, stannous chloride fluoride, stannous acetate, sodium stannous fluoride, stannous hexafluorozirconate, stannous sulfate, stannous tartrate, stannous gluconate, disodium monostannous citrate. Preferred stannous salts include stannous fluoride and stannous chloride.

The stannous may be bound to the phosphopeptide stabilized amorphous calcium phosphate (ACP) and/or amorphous calcium fluoride phosphate (ACFP) as determined using the experimental protocol in Example 2. In one embodiment, stannous-associated PP stabilized amorphous calcium phosphate (ACP) and/or amorphous calcium fluoride phosphate (ACFP) complex are produced by the method as described herein, including but not limited to the method described in Example 1.

In any aspect of the invention, the stannous ion content of a complex of the invention may be equal to, or greater than, 1 mole of stannous per mole of PP but less than 4 moles of stannous per mole of PP. For example, the stannous ion content may be equal to, or greater than about 1.0, 1.2, 1.4, 1.6, 1.8, 2.0, 2.2, 2.4, 2.6, 2.8, 3.0, 3.2, 3.4, 3.6, 3.8 or 4.0 moles of stannous per mole of PP. Also contemplated is a range of stannous ion content between any 2 values of 1.0, 1.2, 1.4, 1.6, 1.8, 2.0, 2.2, 2.4, 2.6, 2.8, 3.0, 3.2, 3.4, 3.6, 3.8 or 4.0.

In any aspect of the invention, the stannous ion content of a complex of the invention may be between about 1 mole of stannous per mole of PP and about 3 moles of stannous per mole of PP.

In any aspect, the stannous ion content of the complex is between about 1 mole of stannous per mole of PP and about 2 moles of stannous per mole of PP. This range includes 1.0, 1.1, 1.2, 1.3, 1.4, 1.5, 1.6, 1.7, 1.8, 1.9 or 2.0 moles of stannous per mole of PP. The stannous ion content of the complex may be about 1 mole of stannous per mole of PP or about 2 moles of stannous per mole of PP.

In any aspect of the invention, the stannous ion content of a complex of the invention may be between about 1.2 moles of stannous per mole of PP and about 1.8 moles of stannous per mole of PP. Preferably, the stannous ion content is between about 1.4 moles of stannous per mole of PP and about 1.8 moles of stannous per mole of PP; or between about 1.3 moles of stannous per mole of PP and about 1.5 moles of stannous per mole of PP. Most preferably, the stannous ion content of the complex is about 1.6 moles of stannous per mole of PP.

A composition of the invention may also have a stannous ion content that is equivalent to a complex of the invention. For example, a composition of the invention may have a stannous ion content of 1.6 moles of stannous per mole of PP. Accordingly, reference to a stannous ion content of a complex as used herein may also refer to the stannous ion content of a composition.

The amount of stannous in a complex or composition may be determined by any method as described herein, or known in the art.

In any aspect, the present invention is applied to a dental surface of an oral site which may be dental enamel or dentine. Typically, the surface is exposed dentine which may be exposed as a result of loss of enamel or cementum. The exposed dentine is preferably causing dentinal hypersensitivity. The exposed dentine as a result of a breach of cementum may be identified by gingival recession and exposure of the root surface to the oral environment. Typically, the oral site is on a molar.

Typically, the exposed dentine contains dentinal tubules with openings greater than 1.0, 1.2, 1.4, 1.6, 1.8, 2.0, 2.2, 2.4, or 2.5 μm in diameter.

An individual suffering from dentinal sensitivity, preferably hypersensitivity, may be one that experiences pain when an area of a tooth is exposed to thermal or tactile stimuli. Specifically, the individual may experience pain when an area of a tooth comes into contact with cold air, hot and cold liquids, foods that are sweet or acidic, or is touched with a metal object. In any aspect, an individual may be identified for treatment by exposure to any one of these stimuli prior to treatment to determine whether they experience a pain sensation. An individual with tooth hypersensitivity may be identified as having a larger number of open dentinal tubules and/or tubules with a larger in diameter than normal, for example the individual may have, or have a greater number of, dentinal tubules with openings greater than 1.0, 1.2, 1.4, 1.6, 1.8, 2.0, 2.2, 2.4, or 2.5 μm in diameter.

The words 'treat' or 'treatment' refer to therapeutic treatment wherein the object is to slow down (lessen) an undesired physiological change or disorder. For purposes of this invention, beneficial or desired clinical results include, but are not limited to, alleviation of symptoms, diminishment of extent of the condition, stabilized (i.e., not worsening) state of the condition, delay or slowing of condition progression, amelioration or palliation of the disease/condition state, and remission (whether partial or total), whether detectable or undetectable. Treatment may not necessarily result in the complete absence of detectable symptoms of the condition but may reduce or minimise complications and side effects of the condition. The success or otherwise of treatment may be monitored by physical examination of the individual or response to any thermal, tactile or chemical treatment as described herein. Preferably, the individual experiences a reduction in the severity of the pain or a reduction in the incidence of pain over time. Methods for identifying individuals having different degrees of dentinal sensitivity, and for measuring success of treatment or prevention, are described herein and also include those outlined in Med Oral Patol Oral Cir Bucal. 2008 Mar. 1; 13(3):E201-6. Treatment of an individual may be determined by comparing the level of pain experienced when exposed to any stimuli described herein before and after treatment, whereby a reduction in pain after treatment indicates a reduction in sensitivity.

The words 'prevent' and 'prevention' generally refer to prophylactic or preventative measures for protecting or precluding an individual not having sensitivity from progressing to sensitivity. Individuals in whom prevention may be required are those undergoing a dental procedure, particularly a dental procedure that exposes dentine.

In any aspect of the present invention, the stannous ion content above may be the stannous ion content tightly-bound to the complex (as described herein). In assessing the stannous ion content, the tightly-bound stannous ion content is measured by the methods described herein, in particular, in Example 2.

The invention also provides a stannous-associated phosphopeptide stabilized ACP and/or ACFP complex comprising stannous ions that remain associated with the complex after centrifugation in a 1000 molecular weight cut off filter at about 3000 g for 1 hour at room temperature, wherein the stannous ion content that remains associated with the complex is equal to, or greater than, 1 mole of stannous per mole of PP but less than 4 moles of stannous per mole of PP.

The invention also provides a stannous-associated phosphopeptide stabilized ACP or ACFP having at least 50, 60, 65, 70, 75, 80, 85, 90, 91, 92, 93, 94, 95, 96, 97, 98, 99 or 100% of the stannous associated with the complex as tightly bound as determined by the method in Example 2.

In any composition of the invention, the amount of phosphopeptide stabilized ACP or ACFP, preferably CPP-ACP or ACFP, may be between about 2% to 5% and the amount of stannous compound, preferably $SnF_2$, may be 500 ppm F. The phosphopeptide stabilized ACP or ACFP may be 2% or 5%.

In any composition of the invention, the amount of phosphopeptide stabilized ACP or ACFP, preferably CPP-ACP or ACFP, may be equal to, or greater than, about 0.1, 0.5, 1, 1.5, 2, 2.5, 3, 3.5, 4, 4.5, 5, 5.5, 6, 6.5, 7, 7.5, 8, 8.5, 9, 9.5 or 10% by weight. Typically, the amount of stannous compound, preferably $SnF_2$, may be equal to, or greater than, about 100, 120, 140, 160, 180, 200, 220, 240, 260, 280, 300, 320, 340, 360, 380, 400, 420, 440, 460, 480, 500, 550, 600, 650, 700, 750, 800, 850, 900, 950, 1000, 1050, 1100, 2000, 3000, 4000 or 5000 ppm F.

In one aspect, the present invention provides a method of mineralizing a dental surface or sub-surface comprising contacting the dental surface or subsurface with a stannous-associated phosphopeptide (PP) stabilized amorphous calcium phosphate (ACP) or amorphous calcium fluoride phosphate (ACFP) complex of the invention, or composition of the invention, thereby mineralizing the dental surface or subsurface.

In a preferred embodiment, the stannous-associated phosphopeptide stabilised amorphous calcium phosphate (ACP) or amorphous calcium fluoride phosphate (ACFP) complex has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

In another aspect the invention also provides a composition including stannous-associated phosphopeptide stabilized ACP or ACFP, further comprising fluoride, wherein fluoride is provided as stannous fluoride and/or sodium fluoride. Preferably, there are 2 moles of fluoride for every mole of stannous. Preferably, the composition is toothpaste or any other oral care composition as described herein.

In a preferred embodiment, the calcium ion content of the stannous-associated phosphopeptide stabilised ACP or ACFP complex is in the range of about 30 to 100 moles of calcium per mole of PP. More preferably, the calcium ion content is in the range of about 30 to about 50 moles of calcium per mole of PP.

In a preferred embodiment the stannous-associated phosphopeptide ACP and/or ACFP complex is in the form of a casein phosphopeptide stabilized ACP and/or ACFP complex.

In any aspect of the invention, the phosphopeptide or phosphoprotein is a casein phosphopeptide or phosphoprotein or a tryptic digest thereof.

Preferably, the phase of the ACP is primarily (i.e. >50%) a basic phase, wherein the ACP comprises predominantly the species $Ca^{2+}$, $PO_4^{3-}$ and OH. The basic phase of ACP may have the general formula $[Ca_3(PO_4)_2]_x[Ca_2(PO_4)(OH)]$ where $x \geq 1$. Preferably $x=1$-5. More preferably, $x=1$, i.e. the two components of the formula are present in equal proportions. Accordingly, in one embodiment, the basic phase of ACP has the formula $Ca_3(PO_4)_2Ca_2(PO_4)(OH)$.

Preferably, the phase of the ACFP is a primarily (i.e. >50%) basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)F]_y$ where $x \geq 1$ when $y=1$ or where $y \geq 1$ when $x=1$. Preferably, $y=1$ and $x=1$-3. More preferably, $y=1$ and $x=1$, i.e. the two components of the formula are present in equal proportions. Accordingly, in one embodiment, the basic phase of ACFP has the formula $Ca_3(PO_4)_2Ca_2(PO_4)F$.

A stannous-associated PP stabilized ACP or ACFP complex as referred to herein includes a stannous-associated PP stabilized-ACP or ACFP complex formed at a pH of at, or below, 7.3. Preferably the complex is formed at a pH in the range of about 5.0 up to but below 7.3. More preferably the complex is formed at a pH range of about 4.0 to 7.3, or 5.0 to about 6.0. In one embodiment, the pH during formation is maintained at pH 7.3 or below. In a preferred embodiment, the complex is formed at a pH of about 5.5. Preferably, the ACP or ACFP in the complex is predominantly in a basic form. The stannous-associated stabilized ACP or ACFP complex when produced on an industrial scale may be produced in a bulk solution that may have a pH greater than about 7.3, preferably about 9.0, however the local pH at formation of the complexes is below about 7.3, preferably about 4.0 to 6.5, preferably about 5.5.

When stannous-associated PP stabilized ACP or ACFP, or stabilized ACP or ACFP, is produced in the laboratory, in smaller quantities than commercial production the pH of the entire solution may be maintained at a given pH, i.e. if the CPP-ACP was prepared at pH 5.5, then the entire solution during CPP-ACP formation was maintained at pH 5.5. However, it may be neither necessary nor desirable to reduce the pH of the entire bulk solution in commercial manufacture to 5.5 as the only part of the bulk solution required to have the acidic pH is where the complexes are forming and the bulk solution can have, and does have, localised fluctuations in pH. The pH fluctuations arise particularly from protons provided by the phosphate compound, for example dihydrogen phosphate, as it is added and the protons liberated from acidic phosphate ions when they convert into the basic form, $PO_4^{3-}$. Therefore, while the overall pH of the bulk solution may be at above 7.3, for example about pH 9, the localised pH at which the CPP-ACP is formed is lower, typically below 7.3 or 6.5, preferably about 4.0 to 7.3, more preferably about 5.5. These fluctuations are localised due to the size of the bulk solution.

The present invention also provides a method or process for forming a stannous-associated PP stabilized ACP of the invention is a method comprising the steps of:
(i) obtaining a solution comprising at least one phosphopeptide and;
(ii) admixing solutions comprising calcium ions, phosphate ions and hydroxide ions, while maintaining the pH at about 7.3 or below; and
(iii) admixing a stannous compound;
or
(i) providing a solution of phosphopeptide stabilized ACP; and
(ii) admixing a stannous compound.

The present invention also provides a method or process for forming a stannous-associated PP stabilised ACFP is a method comprising the steps of:
(i) obtaining a solution comprising at least one phosphopeptide and;
(ii) admixing solutions comprising calcium ions, phosphate ions, hydroxide ions and fluoride ions, while maintaining the pH at about 7.3 or below; and
(iii) admixing a stannous compound;
or
(i) providing a solution of phosphopeptide stabilized ACFP; and
(ii) admixing a stannous compound.

The hydroxide ions may be titrated into the solution to maintain the phosphopeptide solution at an essentially constant pH. The calcium and phosphate ions may be titrated into the phosphopeptide solution with constant mixing and at a rate that avoids the formation of a calcium phosphate precipitate in the phosphopeptide solution.

The present invention also provides a method or process for forming a stannous-associated PP stabilized ACP of the invention is a method comprising the steps of:
(i) obtaining a solution comprising at least one phosphopeptide and;
(ii) admixing solutions comprising calcium ions and phosphate ions, while maintaining the pH at about 7.3 or below; and
(iii) admixing a stannous compound;
or
(iv) providing a solution of phosphopeptide stabilized ACP; and
(v) admixing a stannous compound.

Preferably, the method or process does not involve the addition of any base or acid. For example, no hydroxide ions are added separately to the solution comprising calcium ions, phosphate ions or stannous compound.

The present invention also provides a method or process for forming a stannous-associated PP stabilised ACFP of the invention is a method comprising the steps of:
(i) obtaining a solution comprising at least one phosphopeptide and;
(ii) admixing solutions comprising calcium ions, phosphate ions and fluoride ions, while maintaining the pH at about 7.3 or below; and
(vi) admixing a stannous compound;
or
(iii) providing a solution of phosphopeptide stabilized ACFP; and
admixing a stannous compound.

Preferably, the method or process does not involve the addition of any base or acid. For example, no hydroxide ions are added separately to the solution comprising calcium ions, phosphate ions, fluoride ions or stannous compound.

A stannous-associated PP stabilized ACP of the invention may be produced by a method comprising the step of admixing CPP-ACP and a stannous compound in an aqueous solution, while maintaining the pH at about 7.3 or below.

A stannous-associated PP stabilized ACFP of the invention may be produced by a method comprising the step of admixing CPP-ACFP and a stannous compound in an aqueous solution, while maintaining the pH at about 7.3 or below.

A stannous-associated PP stabilized ACP of the invention may be produced by a method comprising the steps of:
(i) obtaining a solution comprising CPP-ACP; and;
(ii) admixing a stannous compound, while maintaining the pH at about 7.3 or below.

A stannous stabilised ACFP of the invention may be produced by a method comprising the steps of:
(i) obtaining a solution comprising CPP-ACFP; and;
(ii) admixing a stannous compound, while maintaining the pH at about 7.3 or below.

Preferably, the stannous compound is stannous fluoride. Optionally, the methods of producing stannous-associated PP stabilized ACP or stannous-associated PP stabilized ACFP further comprise admixing sodium fluoride in step (ii).

If necessary, the pH can be maintained with an acid, such as HCl.

Preferably the solution comprising CPP-ACP or CPP-ACFP is prepared by adding CPP-ACP or CPP-ACFP to distilled or deionised water. When a solution comprising 2% or greater, preferably 5%, CPP-ACP or CPP-ACFP is used there is no requirement for the addition of any base or acid during the method or process.

A stannous-associated PP stabilized amorphous calcium phosphate (ACP) and/or amorphous calcium fluoride phosphate (ACFP) complex of the invention may be formed by mixing stabilized PP amorphous calcium phosphate (ACP) and/or amorphous calcium fluoride phosphate (ACFP) complex with stannous fluoride.

In any method described herein for producing a stannous-associated PP stabilized amorphous calcium phosphate (ACP) and/or amorphous calcium fluoride phosphate (ACFP) complex, the amount of phosphopeptide stabilized ACP or ACFP, preferably CPP-ACP or ACFP, may be greater than, or equal to, 2% or 5% and the amount of stannous compound, preferably $SnF_2$, may be greater than or equal to 500 ppm F.

Figure 2:
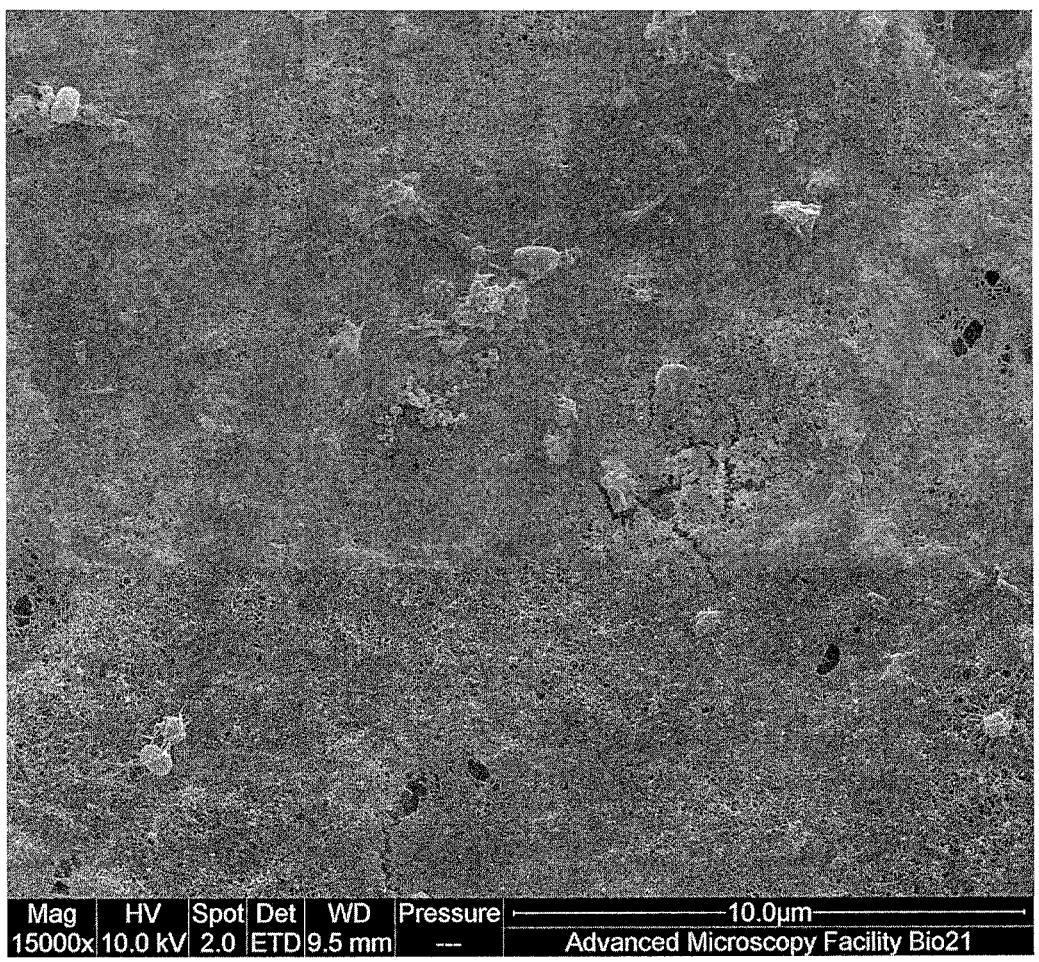
FIG. 2. SEM of patient's dentine tubules treated with Sn/CPP molar ratio 1.6:1 showing self-assembled nanofilaments on the surface of dentine occluding the tubules. Magnification 15,000× and 10 μM scale shown.

A stannous-associated PP stabilized-ACP or ACFP complex as described in the current specification may have the form of a "closed" complex are shown in FIG. 2 of Cross et al., 2007. Current Pharmaceutical Design, 13, 793-800.

A composition comprising a stannous-associated PP stabilized ACP and/or ACFP complex may further include at least an equal amount by weight of calcium phosphate. Preferably the calcium phosphate is $CaHPO_4$. Preferably, the calcium phosphate (e.g. $CaHPO_4$) is dry blended with the PP stabilized ACP and/or ACFP complex. In a preferred embodiment, the PP-ACP and/or PP-ACFP complex:calcium phosphate ratio is about 1:1-50. more preferably about 1:1-25, more preferably about 1:5-15. In one embodiment, the PP-ACP and/or PP-ACFP complex:calcium phosphate ratio is about 1:10.

Preferably, the form of calcium phosphate for dry blending is any soluble calcium phosphate including, but not limited to, $CaHPO_4$, $Ca_2HPO_4$ and calcium lactate.

A composition as described herein may further include free fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

The fluoride ions are preferably present in the composition in an amount greater than 1 ppm. More preferably, the amount is more than 3 ppm. In another embodiment, it is preferably more than 10 ppm. In typical embodiments described below, the amount may be 100 ppm to 5,000 ppm, preferably 400 ppm to 3000 ppm, preferably 1000 ppm to 300 ppm. The fluoride content is typically measured as a ppm in oral compositions in the manner commonly used in the art. Where the fluoride is provided from a source with the stabilized ACP, the ppm refers to the concentration of the fluoride in that source, typically a solution or suspension of bioavailable fluoride.

"Phosphopeptide" in the context of the description of this invention means an amino acid sequence in which at least one amino acid is phosphorylated. Preferably, the phosphopeptide includes one or more of the amino acid sequence-A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys.

In another embodiment, at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

In one embodiment, the ACP or ACFP is stabilized by a casein phosphopeptide (CPP), which is in the form of intact casein or fragment of the casein, and the complex formed preferably has the formula [CPP(ACP)$_8$]$_n$ or [(CPP)(ACFP)$_8$]$_n$ where n is equal to or greater than 1, for example 6. The complex formed may be a colloidal complex, where the core particles aggregate to form large (eg 100 nm) colloidal particles suspended in water. Thus, the PP can be a casein protein or a phosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence-A-B-C- or A-B-C-D-E as described above. The sequence flanking this core sequence may be any sequence. However, those flanking sequences in $\alpha_{s1}$(59-79), $\beta$(1-25), $\alpha_{s2}$(46-70) and $\alpha_{s2}$(1-21) are preferred. The flanking sequences may optionally be modified by deletion, addition or conservative substitution of one or more residues. The amino acid composition and sequence of the flanking region are not critical.

Examples of conservative substitutions are shown in Table 1 below.

TABLE 1

| Original Residue | Exemplary Conservative Substitution | Preferred Conservative Substitution |
|---|---|---|
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Glu | Glu |
| Thr | Ser | Ser |
| Trp | Tyr | Tyr |
| Tyr | Trp Phe Thr Ser | Phe |

The flanking sequences may also include non-naturally occurring amino acid residues. Commonly encountered amino acids which are not encoded by the genetic code, include:

2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2, 3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (AIle) for Ile, Leu, and Val;
p-amidinophenylalanine for Ala;
N-methylglycine (MeGly, sarcosine) for Gly, Pro, Ala.
N-methylisoleucine (MeIle) for Ile;
Norvaline (Nva) for Met and other aliphatic amino acids;
Norleucine (Nle) for Met and other aliphatic amino acids;
Ornithine (Orn) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I)
phenylalanine, triflourylphenylalanine, for Phe.

In one embodiment, the PP is one or more phosphopeptides selected from the group consisting of $\alpha_{s1}$(59-79) [1], $\beta$(1-25) [2], $\alpha_{s2}$(46-70) [3] and $\alpha_{s2}$(1-21) [4]:

[1]
Gln$^{59}$-Met-Glu-Ala-Glu-Ser(P)-Ile-Ser(P)-Ser(P)-

Ser(P)-Glu-Glu-Ile-Val-Pro-Asn-Ser(P)-Val-Glu-

Gln-Lys$^{79}$ $\alpha_{s1}$(59-79)

[2]
Arg$^1$-Glu-Leu-Glu-Glu-Leu-Asn-Val-Pro-Gly-Glu-

Ile-Val-Glu-Ser(P)-Leu-Ser(P)-Ser(P)-Ser(P)-

Glu-Glu-Ser-Ile-Thr-Arg$^{25}$ $\beta$(1-25)

-continued

[3]
Asn$^{46}$-Ala-Asn-Glu-Glu-Glu-Tyr-Ser-Ile-Gly-Ser(P)-

Ser(P)-Ser(P)-Glu-Glu-Ser(P)-Ala-Glu-Val-Ala-

Thr-Glu-Val-Lys$^{70}$ α$_{s2}$(46-70)

[4]
Lys$^{1}$-Asn-Thr-Met-Glu-His-Val-Ser(P)-Ser(P)-

Ser(P)-Glu-Glu-Ser-Ile-Ile-Ser(P)-Gln-Glu-Thr-

Tyr-Lys$^{21}$ α$_{s2}$(1-21).

In another embodiment of the invention, the stannous-associated PP stabilized ACP and/or stannous-associated PP stabilized ACFP complex is incorporated into oral compositions such as toothpaste, mouth washes or formulations for the mouth to aid in the prevention and/or treatment dentinal hypersensitivity. The oral compositions comprising an amount of stannous-associated PP stabilized ACP and/or ACFP sufficient to occlude exposed dentinal tubules or to form a layer over exposed dentinal tubules. The stannous-associated PP stabilized ACP and/or ACFP complexes may comprise 0.01 to 50% by weight of the composition, preferably 1.0 to 50%, preferably 1.0 to 30%, preferably 1.0 to 20%, preferably 1.0 to 10%, preferably 2 to 10% by weight of the composition. In a particularly preferred embodiment, the oral composition of the present invention contains about 2% stabilized ACP or ACFP complexes or a mixture of both.

The oral composition of this invention which contains a complex of the invention may be prepared and used in various forms applicable to the mouth such as dentifrice including toothpastes, toothpowders and liquid dentifrices, mouthwashes, mouthrinses, mouth sprays, varnish, dental cement, troches, chewing gums, dental pastes, gingival massage creams, gargle tablets, dairy products and other foodstuffs including yoghurt. The oral composition according to this invention may further include additional well known ingredients depending on the type and form of a particular oral composition. Certain compositions of the invention such as toothpastes, toothpowders and liquid dentifrices, mouthwashes, mouthrinses and mouth sprays have relatively low viscosity.

A dentifrice or paste for localized application to a sensitive tooth site such as breached cementum of an orally exposed root surface may be one that is applied with a soft applicator. Such a dentifrice or paste may or may not contain conventional abrasive, foaming agent, and flavoring agents.

In certain preferred forms of the invention an oral composition may be substantially liquid in character, such as a mouthwash, rinse or spray. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

In other desirable forms of this invention, the composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic-, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm$^2$/g, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% SiO$_2$, 25.40% MgO, 3.05% Na$_2$O, 0.98%

Li$_2$O, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a jar of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like. The composition of the invention may be a dual phase composition wherein each phase permits release of components over different time periods. For example, in use a dual phase composition may release stannous-associated stabilized ACP and/or stannous-associated stabilized ACFP, preferably CPP-ACP/SnF$_2$ and/or CPP-ACFP/SnF$_2$, from a first phase at a faster rate than a compound that is capable of increasing or maintaining the pH of a solution from a second phase. Preferably, the dual phase composition is a dual phase chewing gum.

An alternative composition may be one that provides phosphopeptide stabilized ACP or ACFP and a stannous compound that then in situ, such as the oral cavity, forms stannous-associated phosphopeptide stabilized ACP or ACFP complexes of the invention. An exemplary composition may be a chewing gum that contains stabilized ACP or ACFP in the pellet and a stannous compound in the centre chew.

Compositions of the invention may be in the form of a gel, liquid, solid, powder, cream or lozenge. Therapeutic compositions may also be in the form of tablets or capsules. In one embodiment, the stannous-associated PP stabilized ACP or ACFP complexes of the invention are substantially the only active components of such a composition. For example, a crème formulation may be employed containing: water; glycerol; complex of the invention; D-sorbitol; silicon dioxide; sodium carboxymethylcellulose (CMC-Na); propylene glycol; titanium dioxide; xylitol; phosphoric acid; guar gum; zinc oxide; sodium saccharin; ethyl p-hydroxybenzoate; magnesium oxide; butyl p-hydroxybenzoate and propyl p-hydroxybenzoate.

The invention further includes a formulation described above provided together with instructions for its use to treat or prevent dentinal hypersensitivity.

In another embodiment, the compositions of the invention as described herein do not include a phosphate buffer and/or a calcium chelator. For example, any dentifrice described herein may not include a phosphate buffer and/or a calcium chelator.

In an embodiment of the present invention there is provided a composition for treating or preventing dentinal hypersensitivity comprising a stannous-associated PP stabilized ACP and/or ACFP complex of the invention, wherein the composition does not include a phosphate buffer and/or calcium chelator.

In another embodiment, the compositions of the invention as described herein do not include a viscosity regulator, or a viscosity regulator at 0.5 to 50%.

In another embodiment, the compositions of the invention as described herein do not include sodium carboxymethylcellulose, or 0.01 to 10% sodium carboxymethylcellulose having the esterification degree of 0.7 to 1.0.

In one embodiment, the active components of the composition consist essentially of the stannous-associated PP stabilized ACP or ACFP complexes of the invention.

In a further aspect, there is provided a method of treating or preventing dentinal hypersensitivity comprising the steps of administering a composition a stannous-associated PP stabilized ACP and/or ACFP complex, to the teeth of a subject. Topical administration of the complex is preferred. The method preferably includes the administration of the complex in a formulation as described above.

In a further aspect there is provided the use of a stannous-associated PP stabilized ACP or ACFP complex of the invention in a manufacture of a composition for the treatment and/or prevention of dental hypersensitivity.

In a further aspect there is provided the use of a stannous-associated PP stabilized ACP or ACFP complex of the invention in a manufacture of a composition for mineralizing a dental surface of subsurface.

According to a further aspect of the invention there is provided a composition for dental restoration, including a dental restorative material to which has been added a stannous-associated PP stabilized ACP or ACFP complex of the invention. The base of the dental restorative material can be a glass ionomer cement, a composite material or any other restorative material which is compatible. A glass ionomer cement is preferred. It is preferred that the amount of stannous-associated PP stabilized ACP or ACFP complexes included in the dental restorative material is 0.01-80% by weight, preferably 0.5-10% and more preferably 1-5% by weight. The dental restorative material of this invention which contains the above mentioned agents may be prepared and used in various forms applicable to dental practice. The dental restorative material according to this embodiment may further include other ions, eg. antibacterial ions $Zn^{2+}$, $Ag^+$, etc or other additional ingredients depending on the type and form of a particular dental restorative material. It is preferable that the pH of dental restorative material according to this embodiment be between 2-10, more preferably 5-9 and even more preferably 5-7. It is preferable that the pH of the dental restorative material containing a stannous-associated stabilized ACP or ACFP complex be in the range of about 2 to 10, more preferably in the range of about 5 to 9 and even more preferably in the range of about 5 to 7.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

One example of a mineralizing composition comprises the following (in decreasing order of proportion):
water
glycerol
CPP-ACP/$SnF_2$
D-sorbitol
silicon dioxide
sodium carboxymethylcellulose (CMC-Na)
propylene glycol
titanium dioxide
xylitol
phosphoric acid
guar gum
zinc oxide
sodium saccharin
ethyl p-hydroxybenzoate
magnesium oxide
butyl p-hydroxybenzoate
propyl p-hydroxybenzoate The invention will now be further described with reference to the following non-limiting examples.

Example 1

Casein phosphopeptide-amorphous calcium phosphate (CPP-ACP) was acquired from Cadbury Enterprises Pte Ltd under the trademark name Recaldent™. Solutions was prepared using CPP-ACP and $SnF_2$ to produce each of the following stannous associated PP stabilized ACP complexes:
 0.4% CPP-ACP+220 ppm F as SnF2 (Sn:CPP molar ratio 8.6:1);
 2% CPP-ACP+500 ppm F as SnF2 (Sn:CPP molar ratio 4:1); and
 5% CPP-ACP+500 ppm F as SnF2 (Sn:CPP molar ratio 1.6:1).

Specifically, the CPP-ACP/$SnF_2$ complexes were prepared by first adding CPP-ACP to distilled/deionised water and then $SnF_2$ (solid or conc solution) added slowly. If the pH needed adjustment it would be adjusted by the addition of 1 M HCl or 1M NaOH to maintain the pH between 4.0-7.3. The pH was not allowed to go above 7.3. There was no pH adjustment needed for when 5% CPP-ACP was used. The total volume of acid/base added was less than 1% of the CPP-ACP/$SnF_2$ solution volume. The final solution contained stannous associated PP stabilized ACP complexes.

Example 2

The following is a protocol for CPP stabilized ACP/$SnF_2$ solution ion analysis. Total (tightly & loosely-bound) and loosely-bound samples were prepared as follows:

Total (tightly and loosely-bound): One ml of any treatment solution 2) to 4) as shown in Example 3 solution can be taken and placed into 19 ml of 1M HNO3 and incubated at room temperature with constant slow end over end mixing for 24 hrs (20 rpm). The mixture is centrifuged at 1000 g for 15 minutes at room temperature. The supernatant is analyzed for calcium, stannous, phosphate and fluoride.

Loosely-bound: A sample of the same solution as for the 'total' analysis immediately above is taken and placed in a centricon with a 1000 MWCO filter and centrifuged at 3000 g for 1 hour at room temperature to produce enough filtrate (<10% of total sample to not affect equilibrium) for analysis by atomic absorption spectrophotometry (AAS) and ion chromatography (IC). The filtrates are then measured to give loosely-bound ions.

The total and loosely bound calcium, stannous, phosphate and fluoride in the solution are determined by ion chromatography (for fluoride and phosphate) and Atomic Absorption Spectrometry (for calcium and stannous).

CPP tightly-bound (colloidal retentate) ions are calculated from the difference between Total and loosely-bound (as explained above).

Example 3

Self-assembly of a nanofilament network on dentine by $SnF_2$/CPP-ACP at a molar ratio of Sn/CPP of 1.6 is superior at occlusion of patent dentine tubules and therefore would be superior at reducing dentinal hypersensitivity.

The hydrodynamic theory of dental hypersensitivity indicates restriction of fluid movement through dentine tubules can result in a clinical reduction of hypersensitivity. Here the inventor shows the synergistic effect of combining CPP-ACP and $SnF_2$ at a Sn(II)/CPP molar ratio of 1.6 on occlusion of tubules of surface dentine using scanning electron microscopy (SEM).

Extracted human third molars were sectioned to create coronal discs approximately 1 mm thick. The discs were covered with acid resistant nail varnish to expose a window of central dentine and were then submerged in 15% EDTA for 2 minutes to remove the smear layer. Discs were randomly allocated to one of four groups and were exposed to the following treatments for 20 min:
1) Double distilled water (DDW) treatment;
2) 0.4% CPP-ACP+220 ppm F as $SnF_2$ (Sn:CPP molar ratio 8.6:1);
3) 2% CPP-ACP+500 ppm F as $SnF_2$ (Sn:CPP molar ratio 4:1); and
4) 5% CPP-ACP+500 ppm F as $SnF_2$ (Sn:CPP molar ratio 1.6:1).

The discs were then dehydrated and sputtered with gold for examination under SEM.

Figure 3:
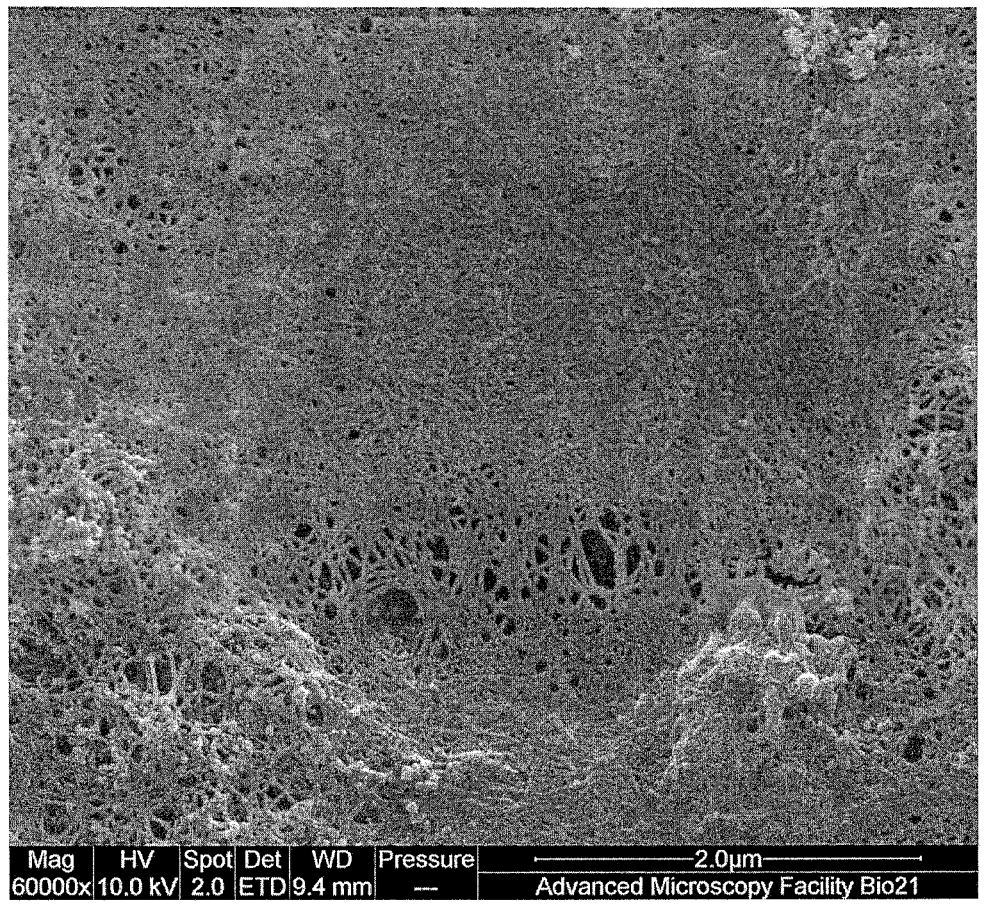
FIG. 3. SEM of patient's dentine tubules treated with Sn/CPP molar ratio 1.6:1 showing self-assembled nanofilaments on the surface of dentine occluding the tubules. A single dentine tubule is shown. Magnification 60,000× and 2.0 μM scale shown.
Figure 4:
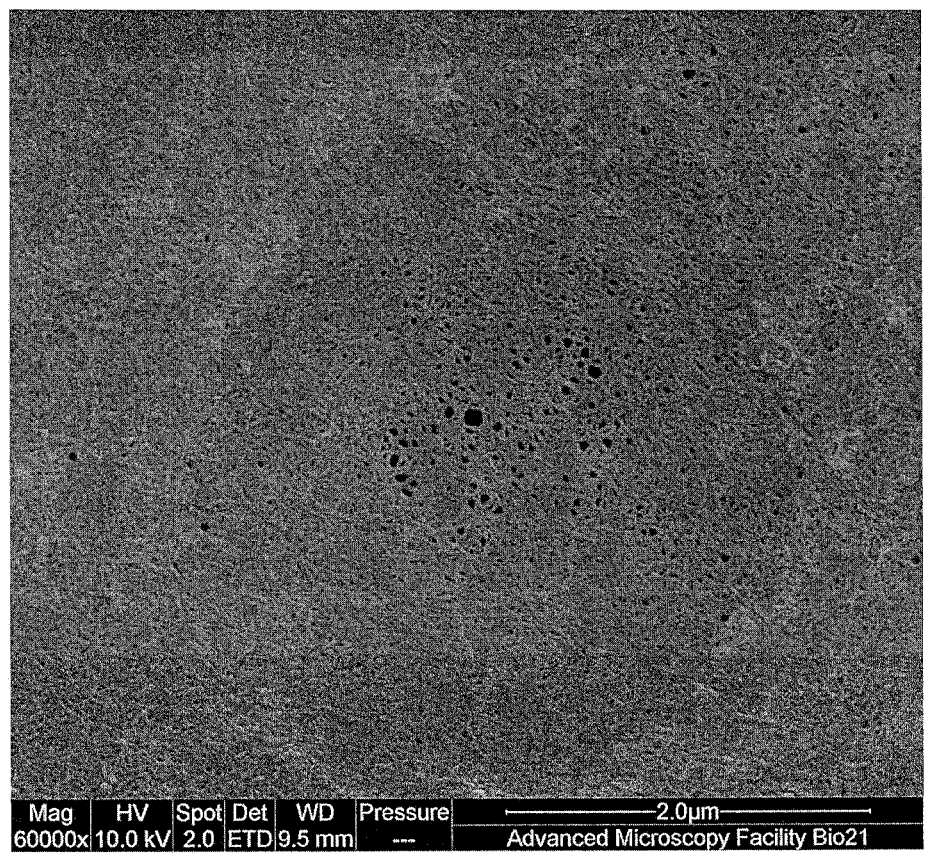
FIG. 4. SEM of patient's dentine tubules treated with Sn/CPP molar ratio 1.6:1 showing self-assembled nanofilaments on the surface of dentine occluding the tubule. A single dentine tubule is shown (a different tubule to that shown in FIG. 3). Magnification 60,000× and 2.0 μM scale shown.
Figure 5:
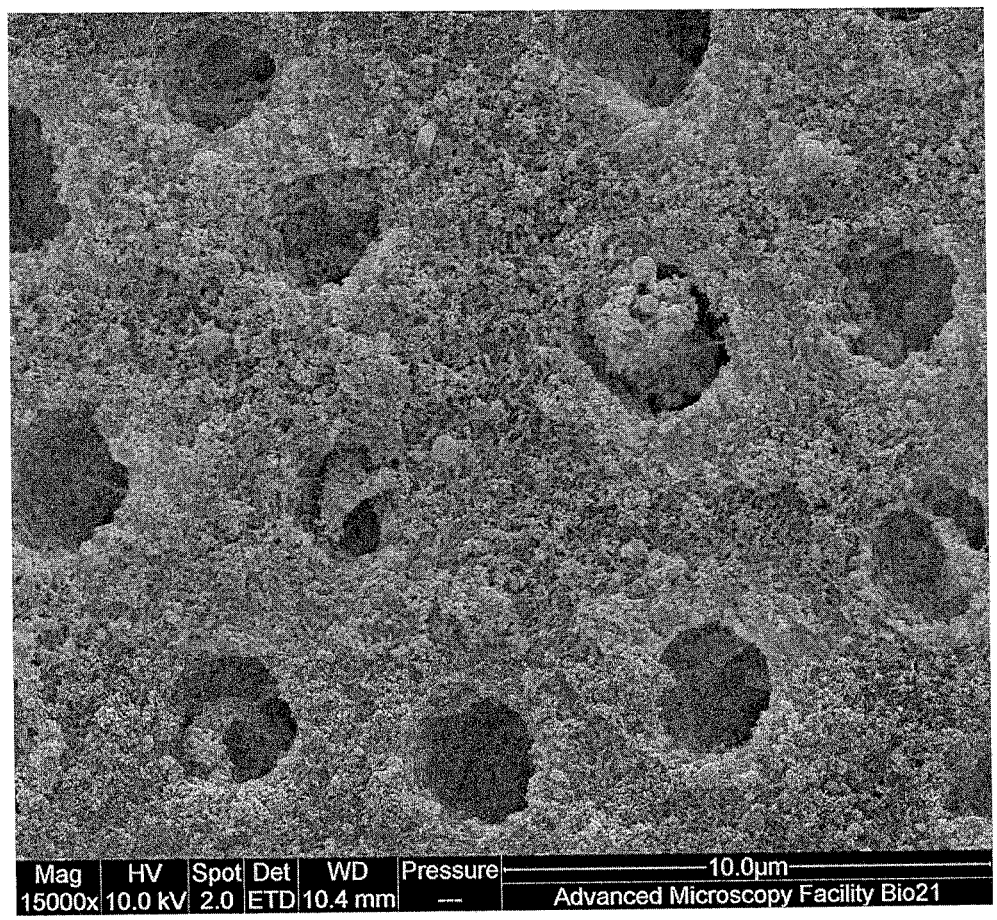
FIG. 5. SEM of patient's dentine tubules treated with Sn/CPP molar ratio 4:1 showing partial formation of self-assembled nanofilaments on the surface of dentine and partial occlusion of tubules. Magnification 15,000× and 10 μM scale shown.
Figure 6:
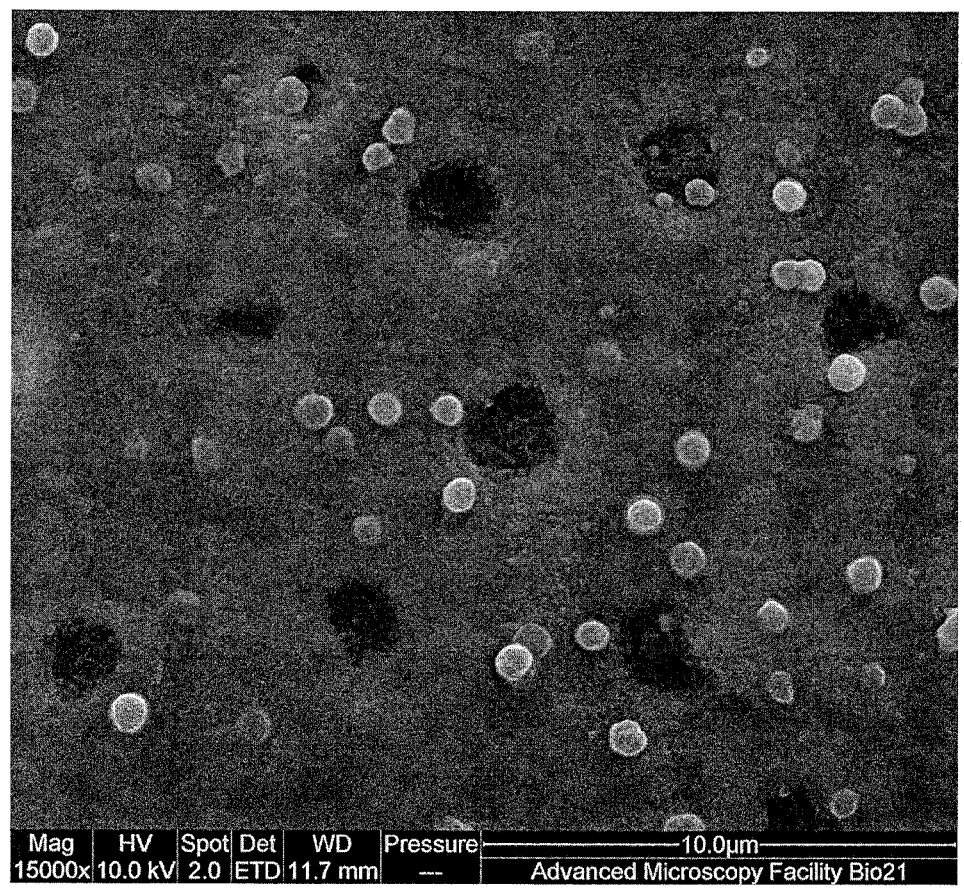
FIG. 6. SEM of patient's dentine tubules treated with Sn/CPP molar ratio 8.6:1 showing partial self-assembled nanofilaments on the surface of dentine and partial occlusion of any tubules. Magnification 15,000× and 10 μM scale shown.

The SEM images in FIGS. 2 to 6 show that dentine exposed to treatments 2 to 4 all exhibited surface precipitation and dentine tubule occlusion to varying degrees. The negative control, DDW treatment, showed smooth dentine surfaces with patent (open) tubules (FIG. 1). The combined 500 ppm F $SnF_2$ and 5% CPP-ACP solution (Sn/CPP molar ratio 1.6) interacted with the dentine surface to result in a unique pattern of surface coverage that displayed a self-assembled network of nanofilaments across the dentine surface occluding the tubules (FIGS. 2 to 4). These nanofilaments are thought to be Sn-cross-linked CPP which have released their cargo of calcium, phosphate and fluoride ions at the surface upon nanofilament formation. Only the Sn/CPP molar ration 1.6 solution resulted in the cross-linked nanofilaments indicating that the molar ratio of equal to, or greater than 1 mole but less than 4 moles of Sn(II) to CPP is critical for the formation of cross-linked nanofilaments and enhanced reduction in dentinal hypersensitivity. Treatment of exposed dentine with a solution having a Sn:CPP molar ratio of 8.6:1 only resulted in partial occlusion of the dentinal tubules (FIG. 6). Likewise, treatment of exposed dentine with a solution having a Sn:CPP molar ratio of 4:1 provided partial occlusion (FIG. 5).

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A stannous-associated phosphopeptide (PP) stabilized amorphous calcium phosphate (ACP) or amorphous calcium fluoride phosphate (ACFP) complex, wherein the complex has a stannous ion content of from 1.4 moles of stannous per mole of PP to 2.0 moles of stannous per mole of PP, wherein the phosphopeptide is a casein phosphopeptide.

2. The complex according to claim 1, wherein the complex has a stannous ion content of about 1.6 moles of stannous per mole of PP.

3. A composition comprising the complex according to claim 1, and a pharmaceutically acceptable carrier, diluent or excipient.

4. The composition according to claim 3, wherein the composition is a formulation selected from the group consisting of dentifrices, mouthwashes, mouthrinses, mouth sprays, varnishes, dental cements, troches, chewing gums, dental pastes, gingival massage creams, gargle tablets, and dairy products.

5. The composition according to claim 4, wherein the composition is a dentifrice selected from the group consisting of toothpastes, toothpowders and liquid dentifrices.

6. A method for treating or preventing dentinal sensitivity in an individual in need thereof having exposed dentine, comprising administering to the individual the complex according to claim 1, thereby treating or preventing dentinal sensitivity in the individual.

7. The method according to claim 6, wherein the individual is suffering from dentinal sensitivity.

8. The method according to claim 7, wherein the dentinal sensitivity is hypersensitivity.

9. The method according to claim 6, further comprising identifying exposed dentinal tubules in the individual.

10. The method according to claim 9, wherein the individual is identified as having dentinal tubules with openings greater than 1.0 μm in diameter.

11. The method according to claim 9, wherein the individual is identified as having dentinal tubules with openings greater than 2.0 μm in diameter.

12. The method according to claim 6, wherein the exposed dentine contains dentinal tubules with openings greater than 1 μm in diameter.

13. A method or process for forming a stannous-associated PP stabilized ACP complex according to claim 1, comprising:
  (i) obtaining a solution comprising at least one phosphopeptide and;
  (ii) admixing solutions comprising calcium ions and phosphate ions, while maintaining the pH at about 7.3 or below; and
  (iii) admixing a stannous compound in an amount to yield a complex having a stannous ion content of from 1.4 moles of stannous per mole of PP to 2.0 moles of stannous per mole of PP; or
  (a) providing a solution of phosphopeptide stabilized ACFP; and
  (b) admixing a stannous compound in an amount to yield a complex having a stannous ion content of from 1.4 moles of stannous per mole of PP to 2.0 moles of stannous per mole of PP, wherein the phosphopeptide is a casein phosphopeptide.

14. The method according to claim 13, wherein method does not involve addition of any base or acid.

15. The method according to claim 13, wherein no hydroxide ions are added separately to the solution comprising calcium ions, phosphate ions or stannous compound.

16. A method for forming a stannous-associated PP stabilized ACFP complex according to claim 1, comprising:
  (i) obtaining a solution comprising at least one phosphopeptide and;
  (ii) admixing solutions comprising calcium ions, phosphate ions and fluoride ions, while maintaining the pH at about 7.3 or below; and
  (iii) admixing a stannous compound in an amount to yield a complex having a stannous ion content of from 1.4 moles of stannous per mole of PP to 2.0 moles of stannous per mole of PP; or
  (a) providing a solution of phosphopeptide stabilized ACFP; and
  (b) admixing a stannous compound in an amount to yield a complex having a stannous ion content of from 1.4 moles of stannous per mole of PP to 2.0 moles of stannous per mole of PP, wherein the phosphopeptide is a casein phosphopeptide.

17. The complex according to claim 1, wherein the complex has a stannous ion content of 1.4 moles of stannous per mole of PP.

18. The complex according to claim 1, wherein the complex has a stannous ion content of 1.8 moles of stannous per mole of PP.

19. The complex according to claim 1, wherein the complex has a stannous ion content of 2.0 moles of stannous per mole of PP.

* * * * *